United States Patent
Nojiri et al.

[11] Patent Number: 5,947,703
[45] Date of Patent: Sep. 7, 1999

[54] CENTRIFUGAL BLOOD PUMP ASSEMBLY

[75] Inventors: Toshihiko Nojiri, Kanagawa; Tsugito Nakazeki, Shizuoka; Teruaki Akamatsu, Kyoto, all of Japan

[73] Assignee: NTN Corporation, Osaka, Japan

[21] Appl. No.: 08/791,560

[22] Filed: Jan. 31, 1997

[30]     Foreign Application Priority Data

Jan. 31, 1996 [JP] Japan .................................. 8-038850
Jan. 31, 1996 [JP] Japan .................................. 8-038851

[51] Int. Cl.⁶ ........................... F04B 17/00; F01D 25/00; F03B 13/00; B63H 1/00
[52] U.S. Cl. ............... 417/420; 417/423.12; 417/423.14; 415/229; 415/900; 416/174
[58] Field of Search ............................. 417/420, 423.12, 417/423.14; 415/229, 900; 416/174

[56]          References Cited

U.S. PATENT DOCUMENTS

| | | |
|---|---|---|
| 3,487,784 | 1/1970 | Rafferty et al. . |
| 3,647,324 | 3/1972 | Rafferty et al. . |
| 3,864,055 | 2/1975 | Kletschke et al. . |
| 3,957,389 | 5/1976 | Rafferty et al. . |
| 3,970,408 | 7/1976 | Rafferty et al. . |
| 4,082,376 | 4/1978 | Wehde et al. ............................ 308/10 |
| 4,242,039 | 12/1980 | Villiard et al. .......................... 415/112 |
| 5,112,202 | 5/1992 | Oshima et al. ....................... 417/423.7 |
| 5,152,679 | 10/1992 | Kanemitsu et al. ................. 417/423.4 |
| 5,288,215 | 2/1994 | Chancellor et al. ................. 417/423.7 |
| 5,332,374 | 7/1994 | Kricker et al. .......................... 417/420 |
| 5,575,630 | 11/1996 | Nakazawa et al. ..................... 417/420 |
| 5,601,418 | 2/1997 | Ohara et al. ............................ 417/420 |

FOREIGN PATENT DOCUMENTS 57-23114  5/1982  Japan .
82/03176  9/1982  WIPO .

Primary Examiner—Charles G. Freay
Assistant Examiner—Paul L. Ratcliffe
Attorney, Agent, or Firm—Burns, Doane, Swecker & Mathis, LLP

[57]          ABSTRACT

A centrifugal blood pump assembly according to one aspect of the invention includes a housing, an impeller adapted to rotate within the housing for feeding blood, an impeller position control device, and an impeller rotation torque generating device. The impeller rotates without contacting the inner surface of the housing when the position control device and torque generating device are operative. Even when the position control device is inoperative, operation of the torque generating device enables rotation of the impeller while a blood flowpath is defined between the surface of the impeller facing the torque generating device and the inner surface of the housing. A centrifugal blood pump assembly according to another aspect of the invention involves a pump including a housing having blood inlet and outlet ports and an impeller adapted to rotate within the housing for feeding blood. The assembly also includes an uncontrolled magnetic bearing arrangement for the impeller, and controlled magnetic bearing arrangement for the impeller. The bearing arrangements are removably mounted to the pump.

43 Claims, 18 Drawing Sheets

CENTRIFUGAL BLOOD PUMP ASSEMBLY

BACKGROUND OF THE INVENTION

1. Field of the Invention

This invention relates to a magnetic bearing type centrifugal blood pump assembly for pumping blood.

2. Prior Art

Several magnetic bearing type pump apparatus for pumping biological fluid such as blood and plasma are known as disclosed in U.S. Pat. No. 5,112,202 and International Publication No. WO 82/3176. These are centrifugal and axial flow turbo pumps of the magnetic bearing type wherein a magnetic member constituting an impeller is position controlled by a magnetic force of an electromagnet so that the impeller may rotate without, contact with any component. These blood pump apparatus have an integral structure that an impeller position control section having an electromagnet and a position sensor (that is, controlled magnetic bearing means) and an impeller rotation torque generating section (that is, uncontrolled magnetic bearing means) are incorporated with a pump housing.

In feeding blood, the most important considerations are to avoid breakage of useful components such as erythrocytes and platelets and to avoid coagulation of blood by reaction with foreign matter. Magnetic bearing type blood pumps having no frictional interface on a surface to come in contact with blood are advantageous in this respect and regarded promising as blood pumps for continuous operation over a long term of the order of months. The magnetic bearing type blood pumps, however, have the problem that the pump is interrupted when a failure occurs in the magnetic bearing means, that is, when the impeller position control section or controlled magnetic bearing means becomes inoperative. Upon such failure, the impeller is magnetically attracted toward the impeller rotation torque generating section or uncontrolled magnetic bearing means, and magnetic attractive forces developed between them prevent the impeller from rotating. Once the pump is interrupted, blood contained therein starts coagulating. It is, therefore, desired to provide the blood pump with a fail-safe mechanism which can maintain rotation of the impeller even when the impeller position control section is inoperative, thereby preventing blood coagulation until the blood pump is replaced by a new one.

It is preferred to minimize thrombus formation within the blood pump during rotation of the impeller enabled by the fail-safe mechanism. In particular, since blood stagnation is likely to occur between the impeller and an inner surface of the pump housing facing the impeller rotation torque generating section, it is necessary to suppress blood stagnation in that area.

Therefore, a first object of the present invention is to provide a centrifugal blood pump assembly which has a fail-safe mechanism allowing the impeller rotation torque generating means or uncontrolled magnetic bearing means to rotate the impeller even when the impeller position control section or controlled magnetic hearing means is inoperative, and minimizes thrombus formation within the blood pump during rotation of the impeller enabled by the fail-safe mechanism.

A second object of the present invention is to provide a centrifugal blood pumps assembly which has a fail-safe mechanism allowing the impeller rotation torque generating means or uncontrolled magnetic hearing means to rotate the impeller even when the impeller position control section or controlled magnetic bearing means is inoperative, and ensures effective rotation of the impeller enabled by the fail-safe mechanism.

As mentioned above, blood transportation requires to avoid damage to useful components such as erythrocytes and platelets and to avoid coagulation of blood by reaction with foreign matter. Magnetic bearing type blood pumps having no frictional interface on a surface to come in contact with blood are advantageous in this respect and regarded promising as blood pumps for continuous operation over a long term of the order of months. However, the conventional blood pump apparatus have an integral structure having electromagnets and sensors combined with the pump body and are thus expensive as disposable blood pumps used in heart surgery completed within several hours or in short term service, for example, of several days. Reuse of such pumps is difficult for the reason of possible infection since the interior comes in contact with blood. The pump apparatus must be discarded in entirety. However, since such used medical instruments are industrial wastes, it is desirable to reduce the amount of used medical instruments discarded when the subsequent disposal is taken into account.

A third object of the present invention is to provide a centrifugal blood pump assembly wherein an impeller rotation torque generating means or uncontrolled magnetic bearing means and an impeller position control section or controlled magnetic bearing means are removably mounted to a blood pump so that only the blood pump which is difficult to reuse may be discarded, and the controlled and uncontrolled magnetic bearing means are reusable. This reduces the amount of used medical instruments discarded as industrial waste.

SUMMARY OF THE INVENTION

According to a first aspect of the invention, there is provided a centrifugal blood pump assembly comprising a centrifugal blood pump comprising a housing having an inlet port and an outlet port for blood and adapted to receive blood therein, and an impeller rotatable in the housing for feeding blood by a centrifugal force developed during rotation; a controlled magnetic bearing means for magnetically supporting the impeller; and an uncontrolled magnetic bearing means for magnetically supporting the impeller. The controlled magnetic bearing means and the uncontrolled magnetic bearing means cooperate such that the impeller rotates while it is held at a predetermined position within the housing. The impeller is rotatable even when the controlled magnetic bearing means is inoperative and the uncontrolled magnetic bearing means is operative. During rotation of the impeller, a blood flowpath is defined between a surface of the impeller on the side of the uncontrolled magnetic bearing means and an inner surface of the housing facing the impeller surface.

According to a second aspect of the invention, there is provided a centrifugal blood pump assembly comprising a centrifugal blood pump comprising a housing having an inlet port and an outlet port for blood and adapted to receive blood therein, and an impeller adapted to rotate within the housing for feeding blood by a centrifugal force developed during rotation; a controlled magnetic bearing means for magnetically supporting the impeller; and an uncontrolled magnetic bearing means for magnetically supporting the impeller. The controlled magnetic bearing means and the uncontrolled magnetic bearing means cooperate such that the impeller rotates while it is held at a predetermined position within the housing. The impeller is rotatable even when the controlled magnetic bearing means is inoperative and the uncontrolled magnetic bearing means is operative. The impeller includes an opening extending through the impeller at the center and a beveled edge at the crossing of the opening with the surface of the impeller facing the uncontrolled magnetic bearing means, the beveled edge increasing its diameter toward the uncontrolled magnetic bearing means. The housing includes a raised portion formed on the inner surface at a position corresponding to the opening of the impeller, the raised portion having a tapered side surface which comes in contact with the beveled edge of the impeller when the controlled magnetic bearing means is inoperative.

According to a third aspect of the invention, there is provided a centrifugal blood pump assembly comprising a centrifugal blood pump comprising a housing having an inlet port and an outlet port for blood and adapted to receive blood therein, and an impeller adapted to rotate within the housing for feeding blood by a centrifugal force developed during rotation; a controlled magnetic bearing means for magnetically supporting the impeller; and an uncontrolled magnetic bearing means for magnetically supporting the impeller. The controlled magnetic bearing means and the uncontrolled magnetic bearing means cooperate such that the impeller rotates while it is held at a predetermined position within the housing. The controlled magnetic bearing means and the uncontrolled magnetic bearing means are removably mounted to the blood pump.

DESCRIPTION OF THE PREFERRED EMBODIMENTS

Several embodiments of the centrifugal blood pump assembly according to the invention are described with reference to the accompanying drawings.

Figure 1:
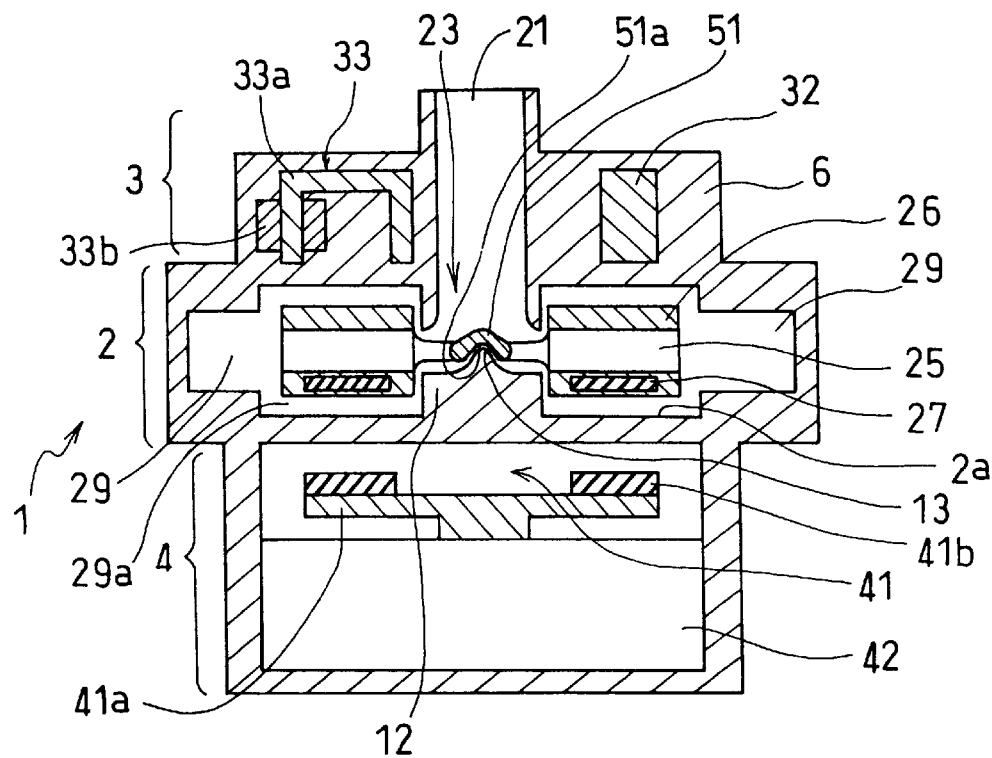
FIG. 1 is a schematic vertical cross-sectional view of a centrifugal blood pump assembly according to a first embodiment of the invention.
Figure 2:
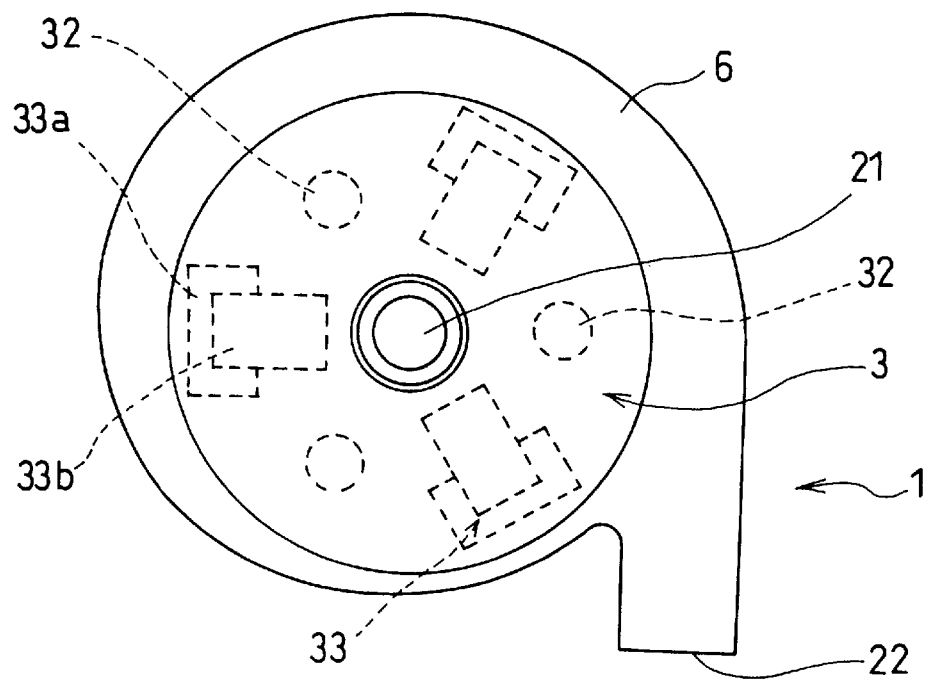
FIG. 2 is a plan view of the pump assembly of FIG. 1.
Figure 3:
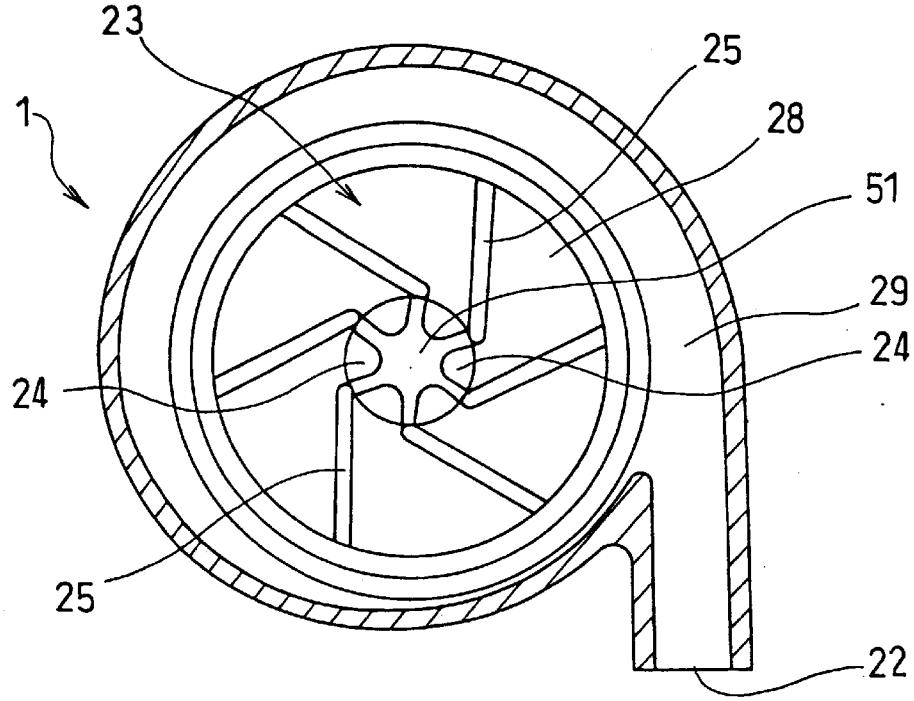
FIG. 3 is a horizontal cross-sectional view of the pump assembly of FIG. 1.
Figure 4:
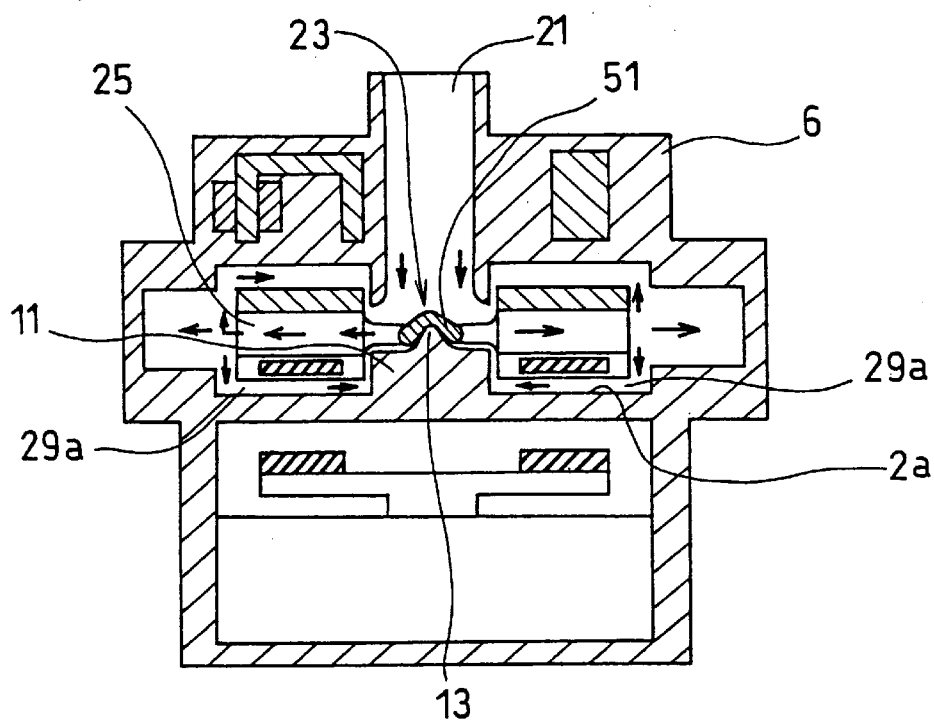
FIG. 4 is a cross-sectional view of the pump assembly similar to FIG. 1 for illustrating its operation.

First referring to FIGS. 1 to 4, a centrifugal blood pump assembly according to a first embodiment of the invention is described. FIG. 1 is a schematic vertical cross-sectional view, FIG. 2 is a plan view of the pump, FIG. 3 is a horizontal cross-sectional view of the pump, and FIG. 4 is a cross-sectional view of the pump for illustrating its operation.

The centrifugal blood pump assembly generally designated at 1 according to the invention includes a centrifugal blood pump 2 comprising a housing 6 having a blood inlet port 21 and a blood outlet port 22 and an impeller 23 received in the housing 6 and adapted to rotate within the housing 6 for feeding blood by a centrifugal force developed during rotation, a controlled magnetic bearing means 3 for magnetically supporting or magnetically suspending the impeller 23 (that is, a section for controlling the position of the impeller, to be simply referred to as an impeller position control section), and an uncontrolled magnetic bearing means 4 for magnetically supporting or magnetically rotating the impeller 23 (that is, a section for generating a torque for rotating the impeller, to be simply referred to as an impeller rotation torque generating section). The controlled magnetic bearing means 3 and the uncontrolled magnetic bearing means 4 cooperate such that the impeller 23 rotates while it is held at a predetermined position within the housing 6. The impeller 23 is rotatable even when the controlled magnetic bearing means 3 is inoperative and the uncontrolled magnetic bearing means 4 is operative. During rotation of the impeller 23, a blood flowpath 29a is defined between a surface of the impeller 23 on the side of the uncontrolled magnetic bearing means 4 and an inner surface of the housing 6 facing the impeller surface.

More particularly, the centrifugal blood pump assembly 1 according to the embodiment illustrated in FIGS. 1 to 4 includes the blood pump 2, the impeller position control section 3, and the impeller rotation torque generating section 4.

The housing 6 has a blood inlet port 21 and a blood outlet port 22 and is formed from a non-magnetic material in a volute shape. The housing 6 defines therein a generally cylindrical chamber or blood flowpath 29a in fluid communication with the inlet and outlet ports 21 and 22. The disc-shaped impeller 23 is accommodated in the chamber 29 of the housing 6. The impeller 23 has one surface (bottom surface in the illustrated embodiment) facing the uncontrolled magnetic bearing means or impeller rotation torque generating section 4 and another surface (upper surface in the illustrated embodiment) facing the controlled magnetic bearing means or impeller position control section 3. The inlet port 21 protrudes from the center of the upper surface of the housing 6 in a substantially vertical direction. The outlet port 22 projects from a side surface of the housing 6 in a tangential direction.

A columnar pedestal 12 is formed nearly at the center of an inner surface of a portion of the housing 6 defining the flowpath 29a (pump housing), that is, a bottom inner surface 2a of the housing 6 facing the lower surface of the impeller 23. The center corresponds to the inlet port 21. A convergent crown 13 protrudes from the upper surface of the pedestal 12 toward the inlet port 21. The crown 13 is seated in a bearing 5 of the impeller 23 to be described later for providing pivotal support to the impeller 23 for rotation.

The impeller 23 is disc-shaped and has a permanent magnet 27 on one surface or lower surface and a magnetic member 26 on another surface or upper surface facing the inlet port 21. The magnetic member 26 is provided such that an electromagnet 33 of the impeller position control section 3 to be described later may attract, the impeller 23 toward the inlet port 21. The permanent magnet 27 is provided such that a permanent magnet 41b on a rotor 41 of the impeller rotation torque generating section 4 to be described later may attract the impeller 23 away from the inlet port 21 and a rotation torque may be transmitted from the impeller rotation torque generating section 4 to the impeller 23. The impeller position control section 3 and the impeller rotation torque generating section 4 constitute a non-contact type magnetic bearing which magnetically attracts the impeller 23 from opposite directions to steadily hold the impeller 23 at a proper position out of contact with the inner surface of the housing 6 so that the impeller 23 may rotate within the housing 6 without contacting its inner surface. The magnetic member 26 may be formed from magnetic stainless steel, nickel or mild steel. The magnetic member 26 is preferably a ring, or a plurality of magnetic strips may be arranged at an equiangular spacing. For the permanent magnet 27, a plurality of magnet strips may be arranged at equal intervals on the lower surface of the impeller 23. Alternatively, a ring may be magnetized to have a plurality of spaced apart magnetic poles.

As shown in FIGS. 1 and 3, the impeller 23 includes a path 24 extending through the impeller 23 near its center corresponding to the inlet port 21 and capable of accommodating the pedestal 12 on the housing 6, a plurality of blades 25 extending tangentially from the periphery of the path 24 to the periphery of the impeller 23, and a bearing 51 formed within the path 24 without blocking the path 24 and having a corresponding plurality of radial arms connected to the blades 25. The bearing 51 on the lower surface has a recess 51a which is convergent toward the inlet port 21 as shown in FIG. 1. The crown 13 of the pedestal 12 on the inner surface of the housing 6 is seated in this recess 5a for bearing purposes. The impeller 23 has a plurality of blood guide channels 28 defined between adjacent blades 25 in fluid communication with the path 24, the inlet port 21 and the flowpath 29 in the housing 6.

In a normal operating state, the impeller position control section 3 and the impeller rotation torque generating section 4 cooperate such that the impeller 23 may rotate within the housing 6 without contact with any inner surface of the housing 6. That is, the bearing recess 51a is out of contact with the crown 13 during normal rotation. If the impeller position control section 3 is interrupted for one reason or another, the impeller 23 is shifted toward the impeller rotation torque generating section 4 as shown in FIG 4. At this point, the crown 13 of the pedestal 12 on the housing 6 is received in the recess 51a of the bearing 51 of the impeller 23. Differently stated, the impeller 23 is pivotally supported at the bearing 51 by the crown 13 and rotates in this state. That is, the recess 51a of the bearing 51 of the impeller 23 and the crown 13 on the housing 6 constitute a pivot bearing. This embodiment minimizes blood damage and thrombus formation by frictional heat since in the event of emergency, frictional sliding occurs during rotation at the center of rotation where the circumferential speed is lowest. Additionally, stable rotation is ensured since the impeller 23 rotates about the crown 13 on the housing 6 so that any side portion of the impeller may not contact the inner surface of the housing 6.

Since the height of the crown 13 from the housing inner surface 2a is greater than the distance between the lower surface of the impeller 23 and the recess 51a of the bearing 51, in the event that the crown 13 on the housing 6 pivotally supports the impeller 23 at its bearing 51 as shown in FIG. 4, the blood flowpath 29a is maintained between the lower surface of the impeller and the inner surface of the housing, preventing blood stagnation between the impeller bottom surface and the housing inner surface and thrombus formation thereby.

Both in the normal state shown in FIG. 1 and during interruption of the impeller position control section 3 shown in FIG. 4, blood flows as shown by arrows in FIG. 4. That is, blood comes in from the inlet port 21, passes through the path 24 and channels 28 of the impeller 23 and then through the flowpath 29 defined between the side of the impeller and the housing inner surfaces, and flows out of the outlet port 22. Part of the blood that has passed the impeller channels 28 enters the flowpath 29a between the lower surface of the impeller 23 and the inner surface 2a of the housing 6 and flows therethrough in a reverse or radially inward direction and back to the channels 28 from a lower portion of the path 24. Maintenance of the flowpath 29a prevents blood stagnation between the impeller lower surface and the housing inner surface 2a.

The impeller position control section 3 includes a plurality of (three in the illustrated embodiment) electromagnets 33 and a plurality of (three in the illustrated embodiment) position sensors 32 both buried in the housing 6. The electromagnets 33 and the position sensors 32 are arranged at equiangular intervals, respectively, while the angle between one electromagnet and an adjacent sensor is also equal. The electromagnet 33 consists essentially of a core 33a and a coil 33b. Three electromagnets 33 are arranged in the illustrated embodiment. More than three electromagnets, for example, four electromagnets may be arranged. By adjusting the electromagnetic forces of the electromagnets 33 in accordance with the results of detection of the position sensors 32 to be described later, forces acting on the impeller in a center axis (z axis) direction can be balanced and moments about x and y axes perpendicular to the center axis (z axis) be zero.

The position sensor 32 detects the distance of a gap between the electromagnet 33 and the magnetic member 26 and produces an output of detection which is fed back to a control (not shown) for controlling electric current to the coil 33b of the electromagnet 33. Even when a radial force as by gravity acts on the impeller 23, the impeller 23 is held at the center of the housing 6 by virtue of shearing forces of a magnetic flux between the permanent magnet 27 of the impeller 23 and the permanent magnet 41b of the rotor 41 and shearing forces of a magnetic flux between the electromagnet 33 and the magnetic member 26.

The impeller rotation torque generating section 4 includes the rotor 41 and a motor 42 for rotating the rotor, the detail of the motor 42 being omitted in the figures. The rotor 41 includes a rotating disc 41a and a plurality of permanent magnets 41b arranged on one surface (upper surface) of the disc 41a facing the blood pump 2. The rotor 41 at the center is fixedly secured to the rotating shaft of the motor 42. A plurality of permanent magnets 41b are arranged at an equiangular spacing so as to correspond to the arrangement (number and position) of the permanent magnets 27 in the impeller 23.

The impeller rotation torque generating section 4 is not limited to the illustrated one including the rotor and motor. For example, a so-called rotor magnet arrangement comprising a plurality of stator coils for attracting the permanent magnets in the impeller for driving the impeller for rotation is acceptable.

Figure 5:
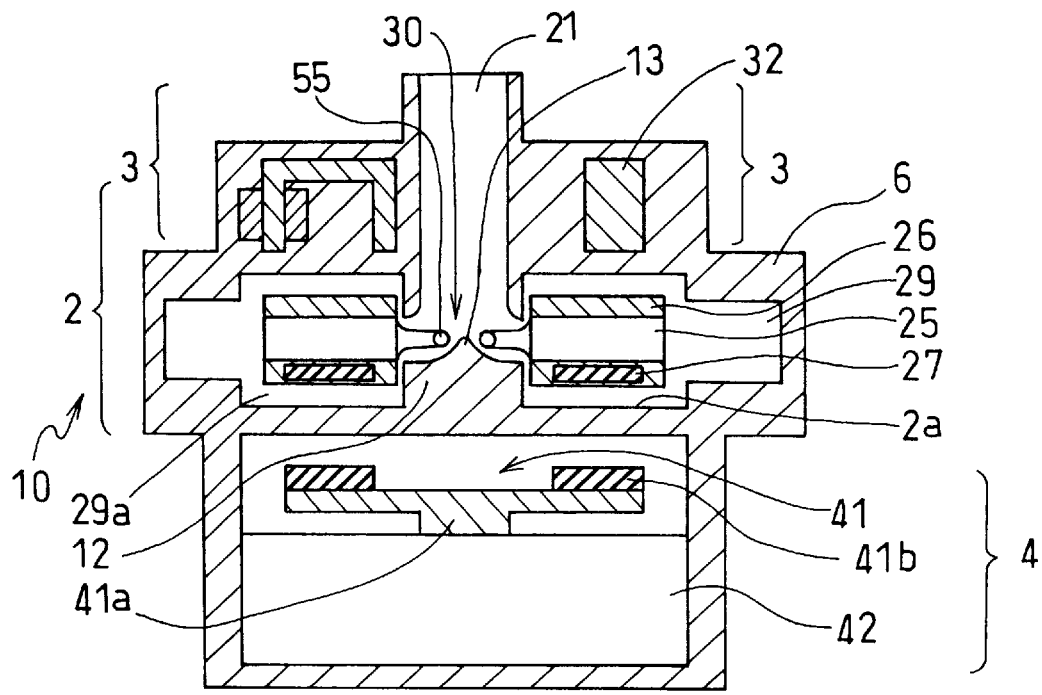
FIG. 5 is a schematic vertical cross-sectional view of a centrifugal blood pump assembly according to a second embodiment of the invention.
Figure 6:
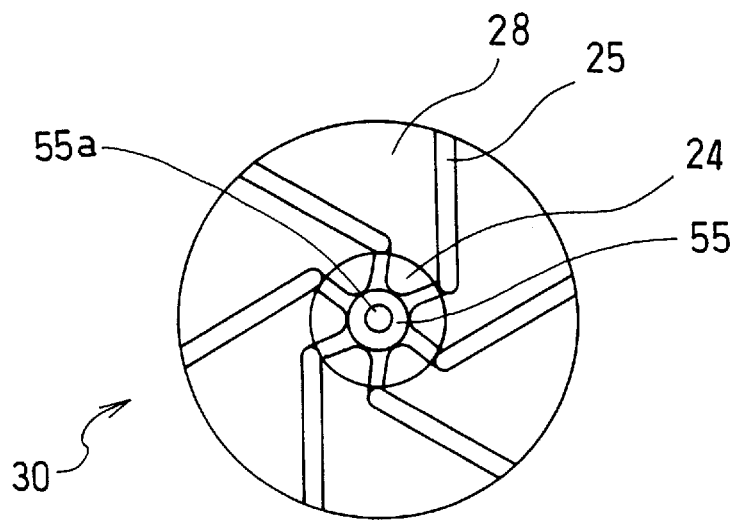
FIG. 6 is a plan view of the impeller used in the pump assembly of FIG. 5.
Figure 7:
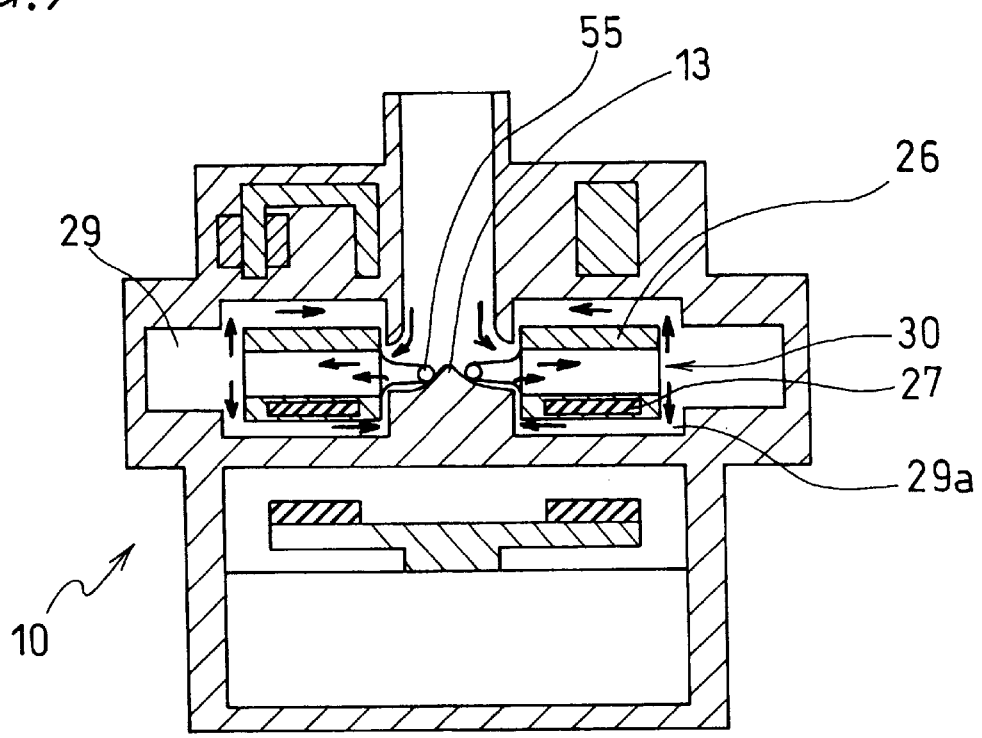
FIG. 7 is a cross-sectional view of the pump assembly similar to FIG. 5 for illustrating its operation.

Referring to FIG. 5 to 7, a centrifugal blood pump assembly 10 according to a second embodiment of the invention is described. The basic construction of the centrifugal blood pump assembly of this embodiment is the same as that of the centrifugal blood pump assembly 1 shown in FIGS. 1 to 4 although the configuration of an impeller is different.

As shown in FIGS. 5 and 6, the impeller 30 includes a path 24 extending through the impeller 30 near its center corresponding to the inlet port 21 and capable of accommodating the pedestal 12 on the housing 6, a plurality of blades 25 extending tangentially from the periphery of the path 24 and then curvilinearly to the periphery of the impeller, and a bearing 55 formed within the path 24 without blocking the path 24 and having a corresponding plurality of radial arms connected to the blades 25. The bearing 55 has a through hole 55a at the center having an inner diameter which is small, but slightly larger than the outer diameter of the crest of the crown 13 on the pedestal 12 as shown in FIG. 6. The inner surface of the through hole 55a bears the crown 13 of the pedestal 12 on the inner surface of the housing 6. The impeller 30 has a plurality of blood guide channels 28 defined between adjacent blades 25 in fluid communication with the path 24, the inlet port 21 and the flowpath 29 in the housing 6.

The height of the crest of the crown 13 from the housing inner surface 2a is greater than the distance between the bottom or lower surface of the impeller 30 to the through hole 55a of the bearing 55. Then even when the crown 13 of the pedestal 12 on the bottom inner surface of the housing 6 bears the impeller 30 at its bearing 55 as shown in. FIG. 7, a blood flowpath 29a is maintained between the lower surface of the impeller 30 and the bottom inner surface of the housing, preventing blood stagnation between the impeller lower surface and the housing bottom inner surface and thrombus formation thereby. Moreover, the through hole 55a at the center of the impeller assists blood in washing away the periphery of the bearing 55, preventing thrombus formation thereat. Furthermore, stable rotation is ensured since the impeller rotates about the crown 13 on the housing 6 without causing the edge of the impeller to contact the housing inner surface.

Figure 8:
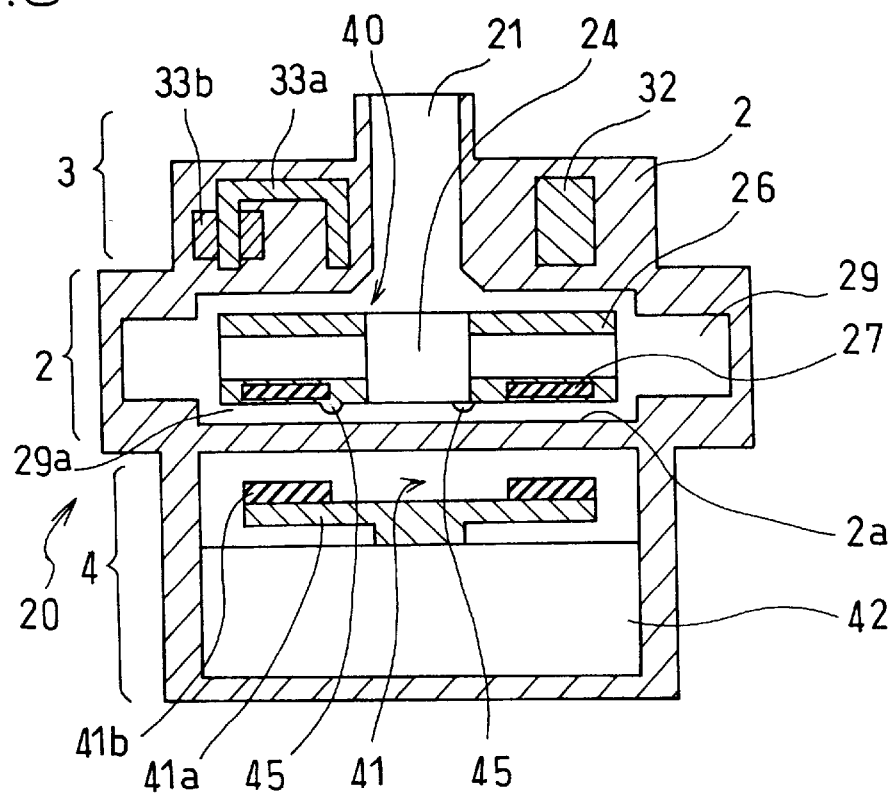
FIG. 8 is a schematic vertical cross-sectional view of a centrifugal blood pump assembly according to a third embodiment of the invention.
Figure 9:
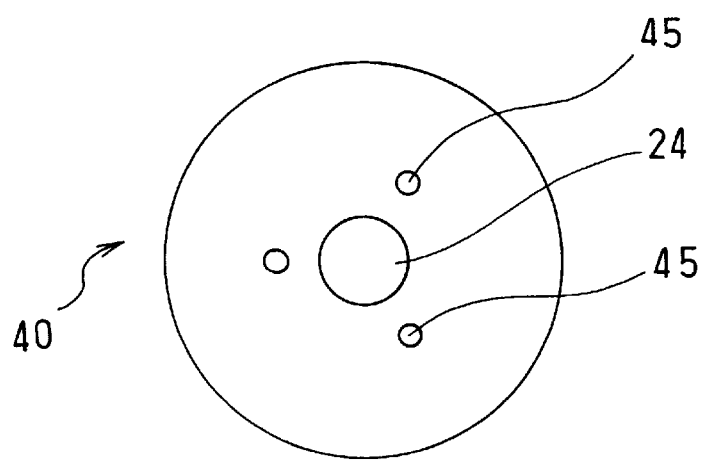
FIG. 9 is a bottom view of the impeller used in the pump of FIG. 8.
Figure 10:
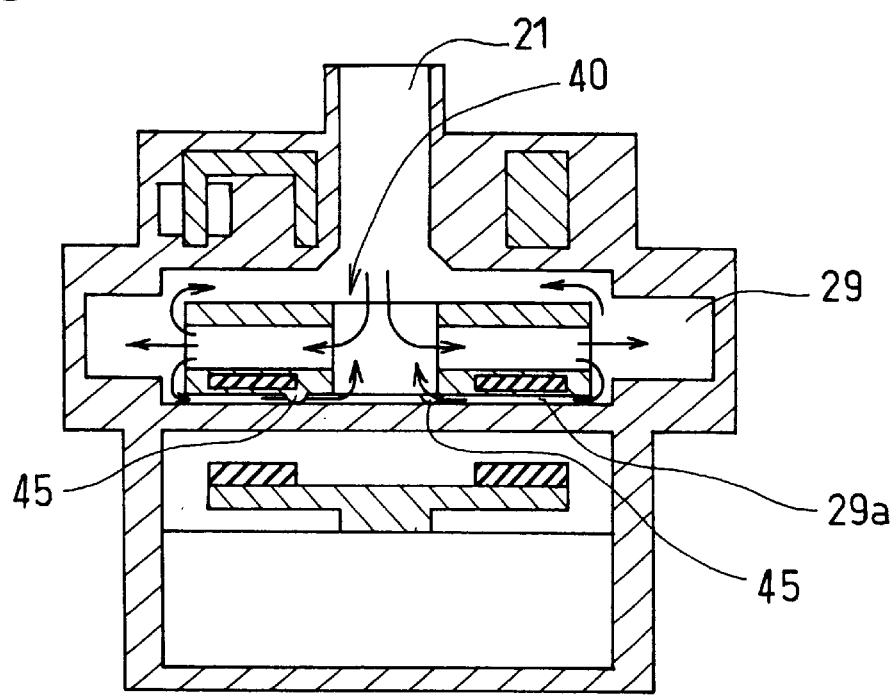
FIG. 10 is a cross-sectional view of the pump assembly similar to FIG. 8 for illustrating its operation.

Referring to FIG. 8 to 10, a centrifugal blood pump assembly 20 according to a third embodiment of the invention is described. The basic construction of the centrifugal blood pump assembly of this embodiment is the same as that of the centrifugal blood pump assembly 1 shown in FIGS. 1 to 4 although the configuration of an impeller and the inner surface configuration of a housing are different.

As shown in FIGS. 8 and 9, the impeller 40 includes a path 24 extending through the impeller 40 near its center corresponding to the inlet port 21, a plurality of blades (not shown) extending tangentially from the periphery of the path 24 and then curvilinearly to the periphery of the impeller, a plurality of blood guide channels (not shown) defined between adjacent blades in fluid communication with the path 24, the inlet port 21 and the flowpath 29 in the housing 6, and a plurality of (at least three) ribs 45 formed on the bottom or lower surface of the impeller. The bottom inner surface 2a of the housing 6 facing the lower surface of the impeller 40 is a flat surface without a pedestal.

Also in this embodiment, even when the impeller 40 rests on the housing bottom inner surface 2a as shown in FIG. 10, the ribs 45 of the impeller 40 maintain a blood flowpath 29a between the lower surface of the impeller 40 and the bottom inner surface of the housing 6, preventing blood stagnation between the impeller lower surface and the housing bottom inner surface and thrombus formation thereby. Additionally, during normal operation, the ribs 45 exert an agitating function between the impeller lower surface and the housing bottom inner surface, preventing local blood stagnation therebetween.

Instead of the ribs 45 on the impeller 40, the bottom inner surface 2a of the housing 6 may be provided with a plurality of (at least three) ribs projecting toward the impeller.

Figure 11:
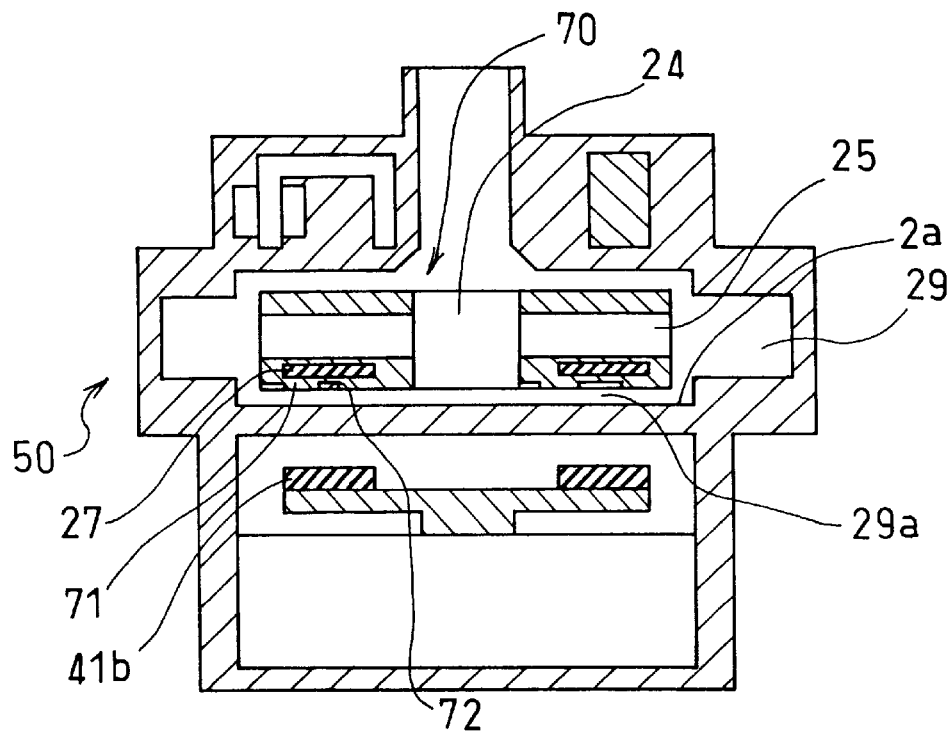
FIG. 11 is a schematic vertical cross-sectional view of a centrifugal blood pump assembly according to a fourth embodiment of the invention.
Figure 12:
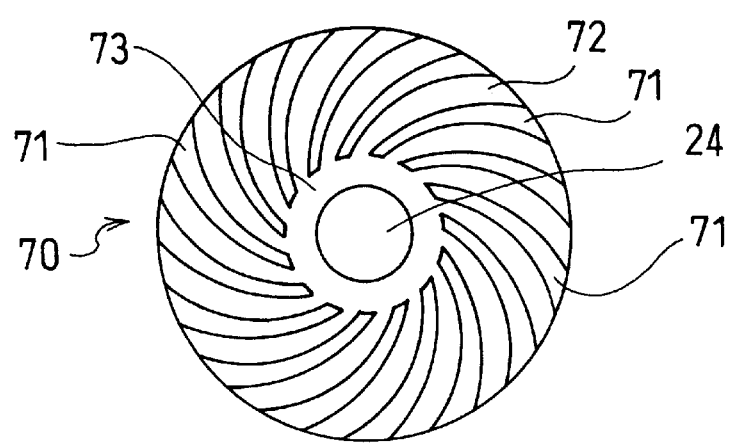
FIG. 12 is a bottom view of the impeller used in the pump of FIG. 11.
Figure 13:
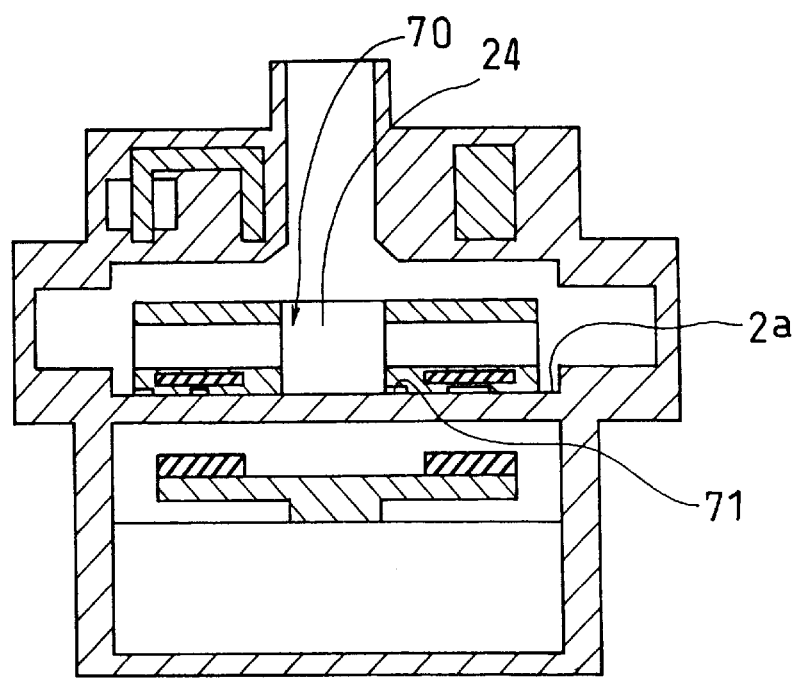
FIG. 13 is a cross-sectional view of the pump similar to FIG. 11 for illustrating its operation.

Referring to FIG. 11 to 13, a centrifugal blood pump assembly 50 according to a fourth embodiment of the invention is described The basic construction of the centrifugal blood pump assembly of this embodiment is the same as that of the centrifugal blood pump assembly 1 shown in FIGS. 1 to 4 although the configuration of an impeller and the inner surface configuration of a housing are different As shown in FIGS. 11 and 12, the impeller 70 includes a path 24 extending through the impeller near its center corresponding to the inlet port 21, a plurality of blades (not shown) extending tangentially from the periphery of the path 24 and then curvilinearly to the periphery of the impeller, a plurality of blood guide channels (not shown) defined between adjacent blades in fluid communication with the path 24, the inlet port 21 and the flowpath 29 in the housing 6, and a plurality of hydrodynamic grooves 71 formed in the bottom or lower surface of the impeller. Each hydrodynamic groove 71 has an inward end on the periphery or circumference of an annular portion 73 slightly spaced from the bottom of the path 24 and extends therefrom to the periphery of the impeller in a volute or curved fashion while its width gradually increases. The plurality of hydrodynamic grooves 71 are formed to substantially the same shape at the same spacing. Lands 72 between adjacent grooves 71 are contiguous to the annular portion 73. The bottom inner surface 2a of the housing 6 facing the lower surface of the impeller 50 is a flat surface without a pedestal.

The hydrodynamic grooves 71 maintain a blood flowpath even when the impeller position control section is inoperative. Although the impeller is attracted (downward) toward the impeller rotation torque generating section when the impeller position control section is inoperative as shown in FIG. 13, a hydrodynamic bearing effect is developed between the hydrodynamic grooves 71 and the bottom inner surface 2a of the housing. Then the impeller is separated from the housing bottom surface, though at a slight spacing, so that the impeller rotates in a contact-free state. That is, a blood flowpath is maintained between the impeller lower surface and the housing bottom inner surface, preventing blood stagnation between the impeller lower surface and the housing bottom inner surface and thrombus formation thereby. Additionally, during normal operation, the hydrodynamic grooves exert an agitating function between the impeller lower surface and the housing bottom surface, preventing local blood stagnation therebetween.

Figure 14:
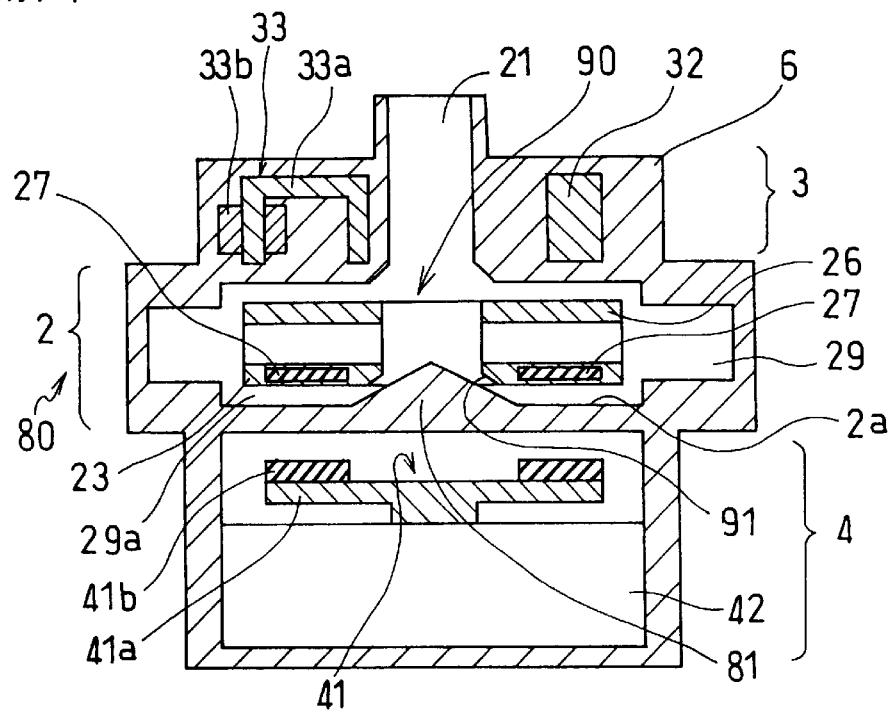
FIG. 14 is a schematic vertical cross-sectional view of a centrifugal blood pump assembly according to a fifth embodiment of the invention.
Figure 15:
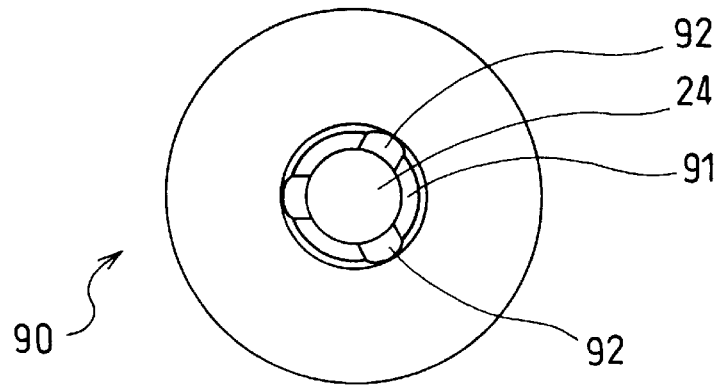
FIG. 15 is a bottom view of the impeller used in the pump of FIG. 14.
Figure 16:
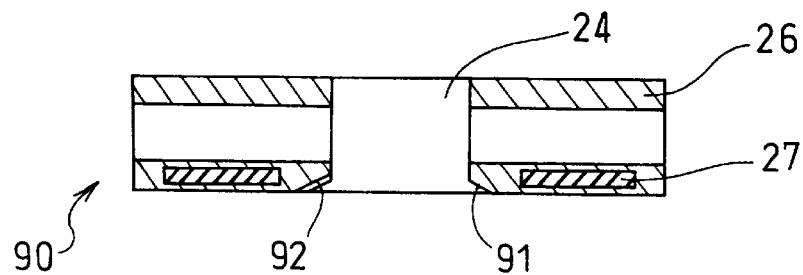
FIG. 16 is a cross-sectional view of the impeller taken along lines Λ—Λ in FIG. 15.

Referring to FIG. 14 to 16, a centrifugal blood pump assembly 80 according to a fifth embodiment of the invention is described. The basic construction of the centrifugal blood pump assembly of this embodiment is the same as that of the centrifugal blood pump assembly 1 shown in FIGS. 1 to 4 although the configuration of an impeller and the inner surface configuration of a housing are different.

As best shown in the bottom view of FIG. 15 and the cross-sectional view of FIG. 16, the impeller 90 of this embodiment includes an opening 24 extending through the impeller near its center and a beveled portion 91 formed at the edge of a surface portion of the impeller facing the impeller rotational torque generating section and adjoining the opening 24, the beveled portion 91 is divergent in an outward or downward direction. The bottom inner surface 2a of the housing 6 is provided with a crown 81 having a slant side surface at a position corresponding to the beveled portion 91 of the impeller 90 so that the crown 81 may contact the beveled portion 91 when the impeller position control section is inoperative.

More particularly, the inner surface of the section of the housing 6 defining the blood flowpath 29 (pump housing), that is, the inner surface 2a of the housing 6 facing the lower surface of the impeller 90 (the surface of the impeller facing the impeller rotation torque generating section) is provided near the center (corresponding to the inlet port 21) with a conical crown 81. The crown 81 is configured such that at least its crest may protrude into the opening 24 of the impeller 90.

As shown in the bottom view of FIG. 15 and the cross-sectional view of FIG. 16, the impeller 90 is configured like a disc and has a magnetic member 26 on one surface or upper surface (facing the blood inlet port) and permanent magnets 27 on another surface or lower surface. The magnetic member 26 is provided such that the impeller may be attracted toward the blood inlet port by means of the electromagnets 33 of the impeller position control section 3.

The impeller 90 includes an opening 24 extending through the impeller near its center corresponding to the inlet port 21, a plurality of blades (not shown) extending tangentially from the periphery of the path 24 and then curvilinearly to the periphery of the impeller, and a plurality of blood guide channels (not shown) defined between adjacent blades in fluid communication with the path 24, the inlet port 21 and the flowpath 29 in the housing 6.

As previously mentioned, the impeller 90 further includes the downwardly divergent beveled portion 91 formed at the periphery of the lower surface of the axial opening 24. The opening 24 is aligned with the crown 81. This beveled portion 91 of the impeller has an angle equal to the angle of the conical crown 81. The beveled portion 91 has an inner diameter which is smaller than the outer diameter of the conical crown 81 at its base. Then this embodiment ensures stable rotation of the impeller 90 when the impeller position control section is inoperative. The beveled portion 91 of the impeller makes substantial plane contact with the conical crown 81 to prevent the lower surface of the impeller from contacting the bottom inner surface of the housing. The impeller rotates in this state, without the risk of the edge of the impeller contacting the inner surface of the housing. Additionally, the beveled portion 91 of the impeller 90 is provided with grooves 92 to prevent blood from stagnating in the space defined between the lower surface of the impeller and the bottom inner surface of the housing, thereby ensuring continuous blood flow therebetween.

Figure 17:
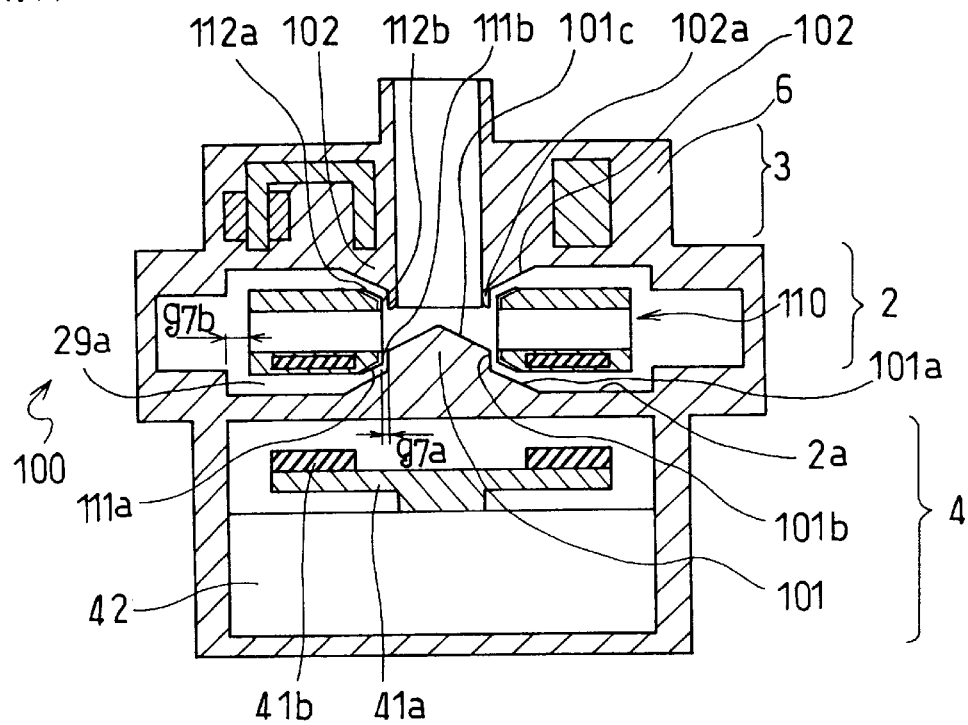
FIG. 17 is a schematic vertical cross-sectional view of a centrifugal blood pump assembly according to a sixth embodiment of the invention.
Figure 18:
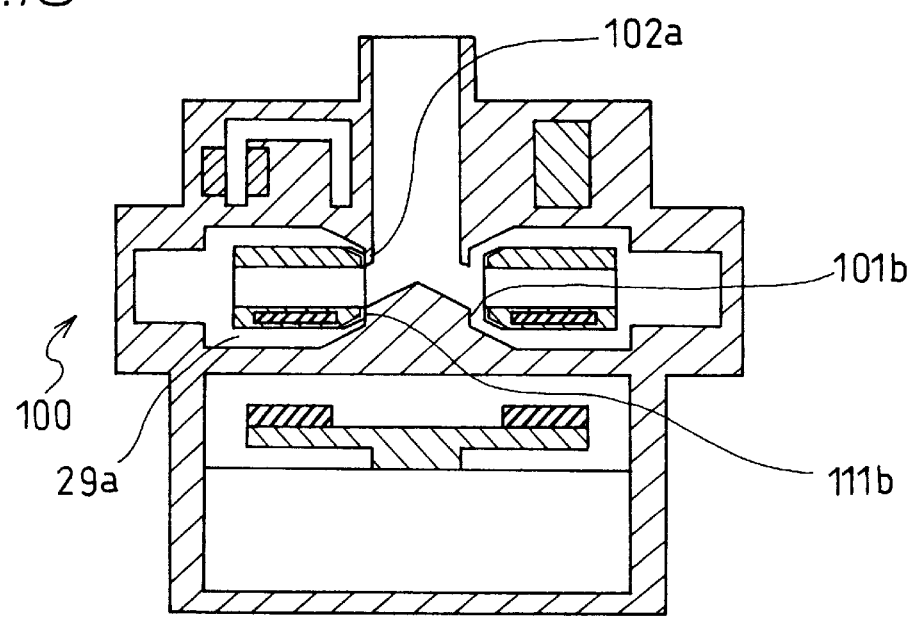
FIG. 18 is a cross-sectional view of the pump assembly similar to FIG. 17 for illustrating its operation.

Referring to FIG. 17 to 18, a centrifugal blood pump assembly 100 according to a sixth embodiment of the invention is described. The basic construction of the centrifugal blood pump assembly of this embodiment is the same as that of the centrifugal blood pump assembly 1 shown in FIGS. 1 to 4 although the configuration of an impeller and the inner surface configuration of a housing are different The impeller 110 of this embodiment includes an opening 24 extending through the impeller near its center, an outwardly divergent beveled portion 111a formed at the edge of the opening 24 on the lower side facing the impeller rotational torque generating section, and an outwardly divergent beveled portion 112a formed at the edge of the opening 24 on the upper side facing the impeller position control section.

On the other hand, the bottom inner surface 2a of the housing 6 is provided with a crown 101 at a position corresponding to the beveled portion 111a of the impeller 110. The crown 101 is aligned with the opening 24. The crown 101 is configured to include a conical base portion 101a having a slant side surface, a cylindrical portion 101b extending upward from the slant side surface, and a conical top portion 101c extending upward from the cylindrical portion 101b. The conical base portion 101a comes in contact with the beveled portion 111a of the impeller when the impeller position control section is inoperative as will be described later. Furthermore, the top inner surface of the housing 6 adjoining the blood inlet port is provided with a raised portion including a tapered portion 102a and a cylindrical rim 102 at a position corresponding to the beveled portion 112a of the impeller 110. The raised portion is also aligned with the opening 24. In this embodiment, the beveled portion 112a of the impeller 110 has an inner diameter which is smaller than the outer diameter of the conical base portion 101a of the crown 101 at the base. Then this embodiment ensures stable rotation of the impeller 110 when the impeller position control section is inoperative. The beveled portion of the impeller 110 makes substantial plane contact with the crown 101 to prevent the lower surface of the impeller from contacting the bottom inner surface of the housing. The impeller rotates in this state, without the risk of the edge of the impeller contacting the inner surface of the housing. If the beveled portion 111a of the impeller 110 is additionally provided with grooves as shown in FIGS. 15 and 16, then the grooves prevent blood from stagnating in the space defined between the lower surface of the impeller and the bottom inner surface of the housing, thereby ensuring continuous blood flow therebetween.

As shown in FIG. 17, a clearance g7a is defined between the inner surface of the opening in the impeller 110 and the cylindrical portion 101b of the crown 101 on the bottom inner surface of the housing. This clearance g7a is narrower than a clearance g7b defined between the housing and the peripheral edge of the impeller 110. Consequently, even if the impeller 110 is displaced by a radial impact force, the impeller 110 comes in contact with the housing at the impeller's inner periphery where the circumferential speed is low. The damage caused by this contact is minimal. Further, in the illustrated embodiment wherein the blood pumping chambers above and below the impeller are symmetrically configured with respect to the impeller center plane, the pressure distributions above and below the impeller are equal to each other independent of variations of flow rate and load so that the impeller receives no axial thrust. This reduces the variation of a load on the electromagnet for controlling magnetic levitation, achieving more stable control of magnetic levitation.

Figure 19:
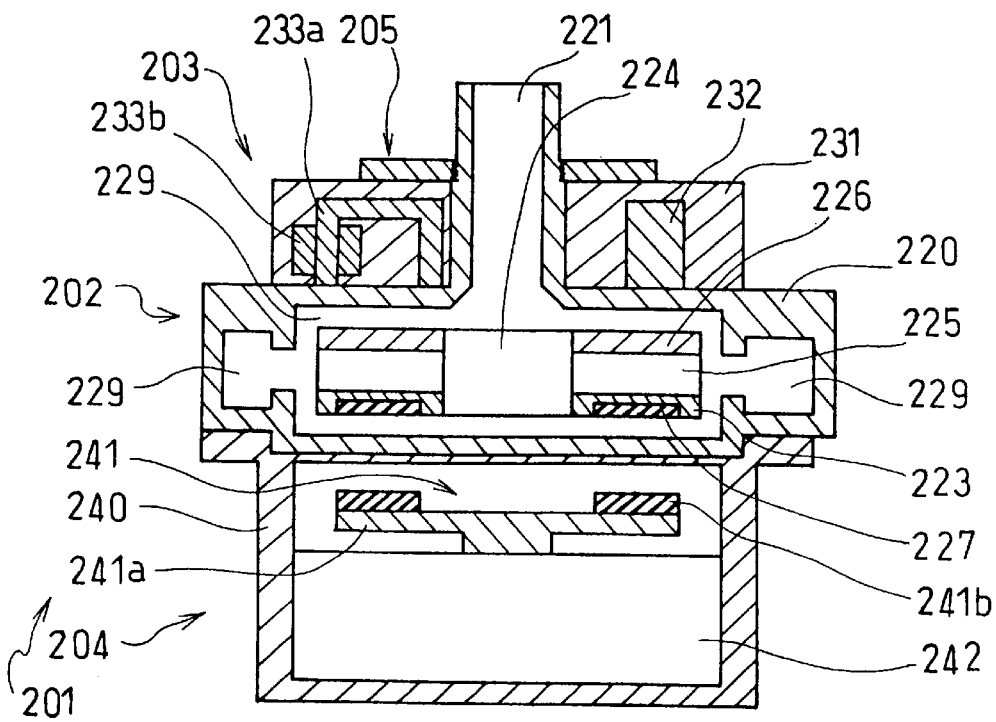
FIG. 19 is a schematic vertical cross-sectional view of a centrifugal blood pump assembly according to a seventh embodiment of the invention.
Figure 20:
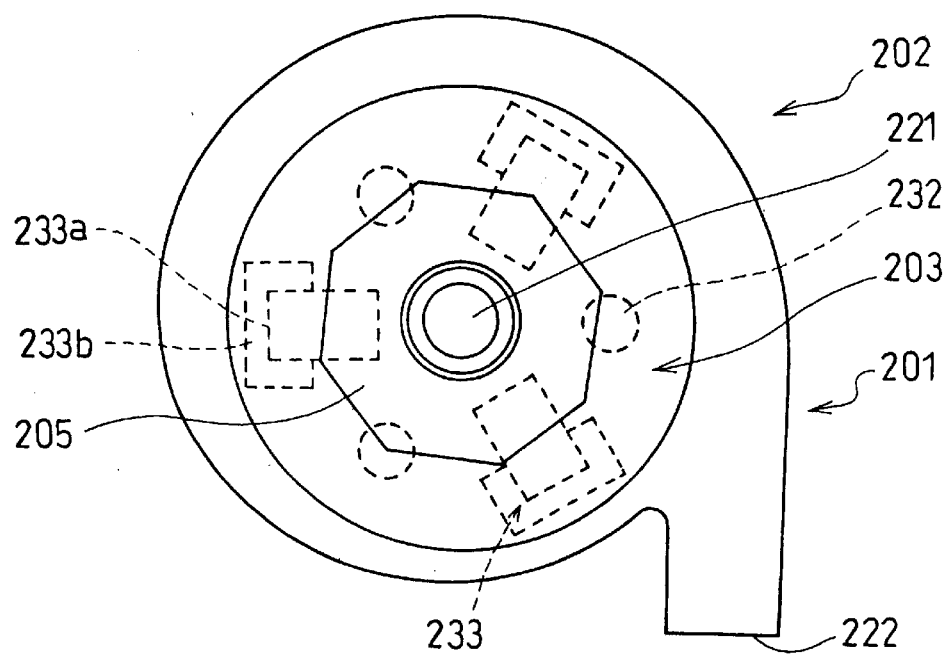
FIG. 20 is a plan view of the pump assembly of FIG. 19.

Referring to FIG. 19, a centrifugal blood pump assembly according to a seventh embodiment of the invention is described.

The centrifugal blood pump assembly 201 of this embodiment includes a centrifugal blood pump 202 comprising a housing 220 having a blood inlet port 221 and a blood outlet port 222 and an impeller 223 received in the housing 220 and adapted to rotate within the housing 220 for feeding blood by a centrifugal force developed during rotation, a controlled magnetic bearing means 203 for magnetically supporting or magnetically suspending the impeller 223 (that is, an unit for controlling the position of the impeller, to be simply referred to as an impeller position control unit), and an uncontrolled magnetic bearing means 204 for magnetically supporting or magnetically rotating the impeller 223 (that is, an unit for generating a torque for rotating the impeller, to be simply referred to as an impeller rotation torque generating unit). The controlled magnetic bearing means 203 and the uncontrolled magnetic bearing means 204 cooperate such that the impeller 223 rotates while it is held at a predetermined position within the housing 220. The controlled magnetic bearing means 203 and uncontrolled magnetic bearing means 204 are removably attached to the pump 202.

Briefly stated, the centrifugal blood pump assembly 201 according to the embodiment illustrated in FIG. 19 includes the blood pump 202, the controlled magnetic bearing means or impeller position (control unit 203, and the uncontrolled magnetic bearing means or impeller rotation torque generating unit 204, with the units 203 and 204 being removably attached to the pump 202.

More particularly, the centrifugal blood pump assembly 201 according to the embodiment illustrated in FIGS. 19 to 22 includes the blood pump 202, the impeller position control unit 203, an attachment member 205 for securing the unit 203 to the pump 202, and the impeller rotation torque generating unit 204.

Figure 22:
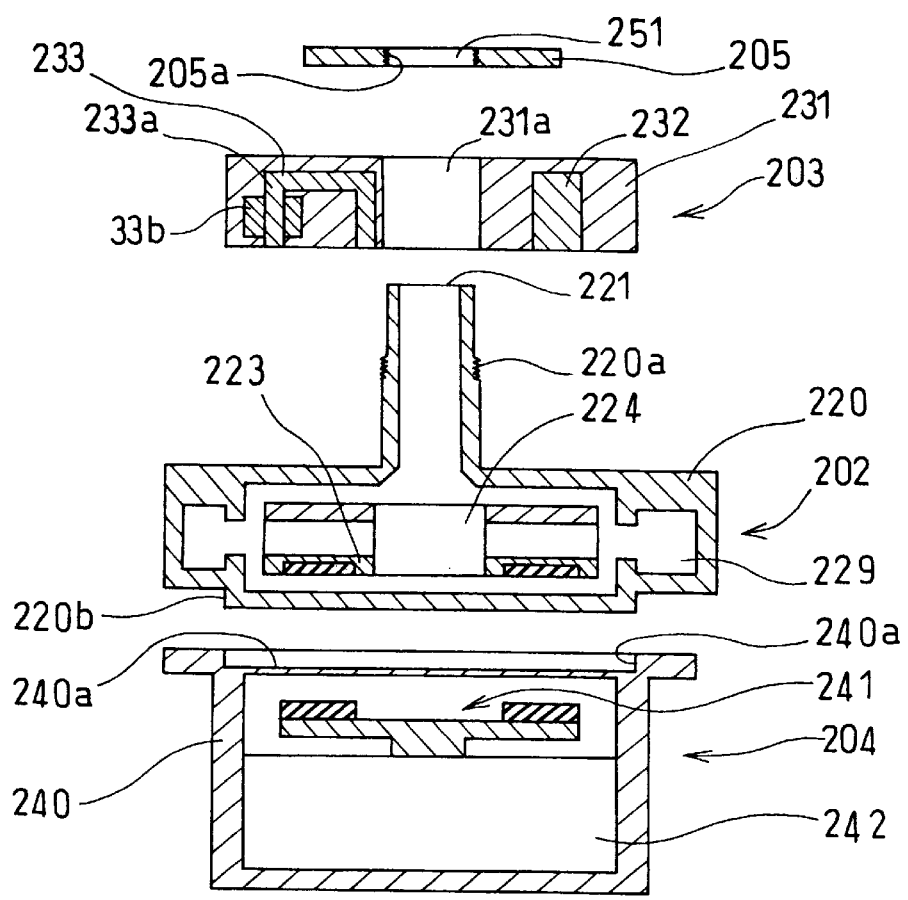
FIG. 22 is an exploded cross-sectional view of the pump assembly of FIG. 19.

As best shown in FIG. 22, the blood pump 202 includes a volute pump housing 220 having a blood inlet port 221 and a blood outlet port 222 and an impeller 223 received in the housing 220. The housing 220 defines therein a generally cylindrical chamber or blood flowpath 229 in fluid communication with the inlet and outlet ports 221 and 222. The inlet port or nozzle 221 on the side surface at an axial intermediate position is provided with external threads 220a for engagement with internal threads 205a in the attachment member 205. The inlet port 221 protrudes from the top surface of the housing 220 near the center of its generally cylindrical portion in a substantially vertical direction. The outlet port 222 projects from a side surface of the volute housing 220 in a tangential direction. The bottom of the housing 220 is stepped to form a disc-shaped projection 220b for engagement with the impeller rotation torque generating unit 204.

The impeller 223 is disc-shaped and accommodated in the chamber 229 of the housing 220. The impeller 223 has one surface (bottom surface in the illustrated embodiment) facing the uncontrolled magnetic bearing means or impeller rotation torque generating unit 204 and another surface (top surface in the illustrated embodiment) facing the controlled magnetic bearing means or impeller position control unit 203.

The impeller 223 has a permanent magnet 227 on one surface or bottom surface and a magnetic member 226 on another surface or top surface facing the inlet port 221. The magnetic member 226 is provided such that an electromagnet 233 of the impeller position control unit 203 to be described later may attract the impeller 223 toward the inlet port 221. The permanent magnet 227 is provided such that a permanent magnet 241b on a rotor 241 of the impeller rotation torque generating unit 204 to be described later may attract the impeller 223 away from the inlet port 221 and a rotation torque may be transmitted from the impeller rotation torque generating unit 204 to the impeller 223. The impeller position control unit 203 and the impeller rotation torque generating unit 204 constitute a non-contact type magnetic bearing which magnetically attracts the impeller 223 from opposite directions to steadily hold the impeller 223 at a proper position out of contact with the bottom inner surface of the housing 220 so that the impeller 223 may rotate within the housing 220 without contacting the housing inner surface. The magnetic member 226 may be formed from magnetic stainless steel, nickel or mild steel. The magnetic member 226 is preferably a ring, or a plurality of magnetic strips may be arranged at an equiangular spacing. For the permanent magnet 227, a plurality of magnet strips may be arranged at an equiangular spacing on the bottom surface of the impeller 223. Alternatively, a ring may be magnetized to have a plurality of spaced apart magnetic poles.

Figure 21:
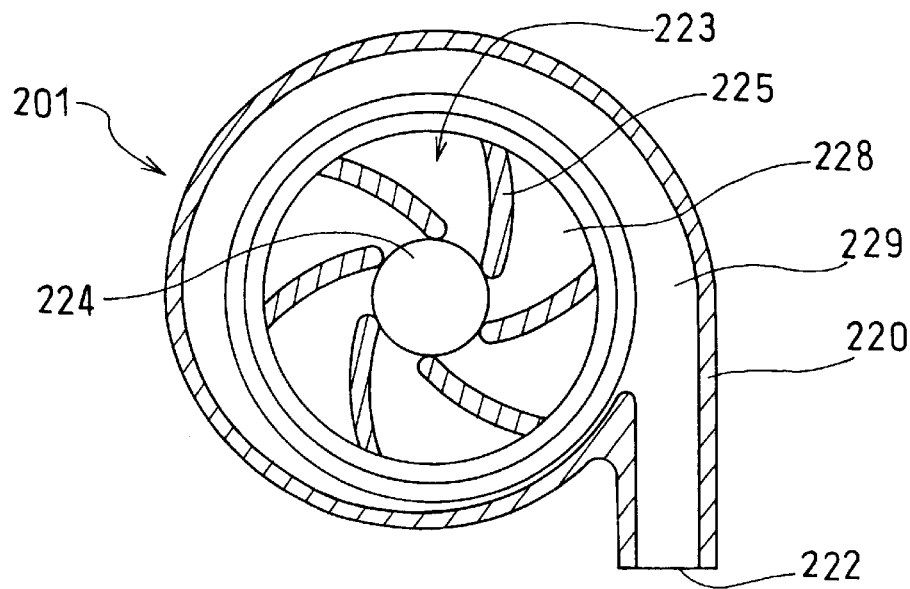
FIG. 21 is a horizontal cross-sectional view of the pump assembly of FIG. 19.

As shown in FIGS. 19 and 21, the impeller 223 includes an opening 224 extending through the impeller near its center corresponding to the inlet port 221, a plurality of blades 225 extending tangentially from the periphery of the opening 224 and then curvilinearly to the periphery of the impeller, and a plurality of blood guide channels 228 defined between adjacent blades 225 in fluid communication with the opening 224, the inlet port 221 and the flowpath 229 in the housing 220.

As shown in FIGS. 19 and 22, the impeller position control unit 203 includes a separate housing 231, a plurality of electromagnets 233, and a plurality of position sensors 232, both buried in the housing 231. The housing 231 has a bore 231a through which the blood inlet port 221 vertically projecting from the housing 220 of the blood pump 202 can be extended. Then the unit 203 can be mounted on the top of the blood pump 202 from above and removed therefrom. When the unit 203 is mounted on the blood pump 202, the external threads 220a on the inlet port 221 extending from the housing 220 of the pump 202 are positioned near the upper surface of the unit 203. Then by fitting the attachment member 205 of a plate shape (typically polygonal plate) having the internal threaded opening 251 on the inlet port 221 of the housing 220 to provide engagement between threads 205a and 220a, the unit 203 is fixedly clamped between the attachment member 205 and the pump 202. Inversely, the unit 203 can be detached from the pump 202 by disengaging the attachment member 205.

The impeller position control unit 203 includes a plurality of (three in the illustrated embodiment) electromagnets 233 and a plurality of (three in the illustrated embodiment) position sensors 232. The electromagnets 233 and the position sensors 232 are arranged at equiangular intervals, respectively, while the angle between one electromagnet and an adjacent sensor is also equal. The electromagnet 233 consists essentially of a core 233a and a coil 233b. Three electromagnets 233 are arranged in the embodiment shown in FIG. 20. More than three electromagnets may be arranged. By adjusting the electromagnetic forces of the electromagnets 233 in accordance with the results of detection of the position sensors 232 to be described later, forces acting on the impeller in a center axis (z axis) direction can be balanced and moments about x and y axes perpendicular to the center axis (z axis) be zero.

The position sensor 232 detects the distance of a gap between the electromagnet 233 and the magnetic member 226 and produces an output of detection which is fed back to a control (not shown) for controlling electric current to the coil 233b of the electromagnet 233. Even when a radial force as by gravity acts on the impeller 233, the impeller 223 is held at the center of the housing 220 by virtue of shearing forces of a magnetic flux between the permanent magnet 227 of the impeller 223 and the permanent magnet 241b of the rotor 241 and shearing forces of a magnetic flux between the electromagnet 233 and the magnetic member 226.

As shown in FIGS. 19 and 22, the impeller rotation torque generating unit 204 includes a separate housing 240 and an impeller rotation torque generating mechanism received therein. The housing 240 is provided at the top surface with a circular recess 240a configured to engage with the bottom projection 220b of the pump 202. By engaging the bottom projection 220b of the pump 202 with the recess 240a in the housing 240 in close fit relationship, the unit 204 can be attached to the blood pump 202. Inversely, the unit 204 can be readily detached from the blood pump 202 by canceling the engagement.

The impeller rotation torque generating mechanism includes the rotor 241 and a motor 242 for rotating the rotor, the detail of the motor 242 being omitted in the figures. The rotor 241 includes a rotating disc 241a and a plurality of permanent magnets 241b arranged on one surface (upper surface) of the disc 241a facing the blood pump 202. The rotor 241 at the center is fixedly secured to the rotating shaft of the motor 242. A plurality of permanent magnets 241b are arranged at an equiangular spacing so as to correspond to the arrangement (number and position) of the permanent magnets 227 in the impeller 223.

Figure 23:
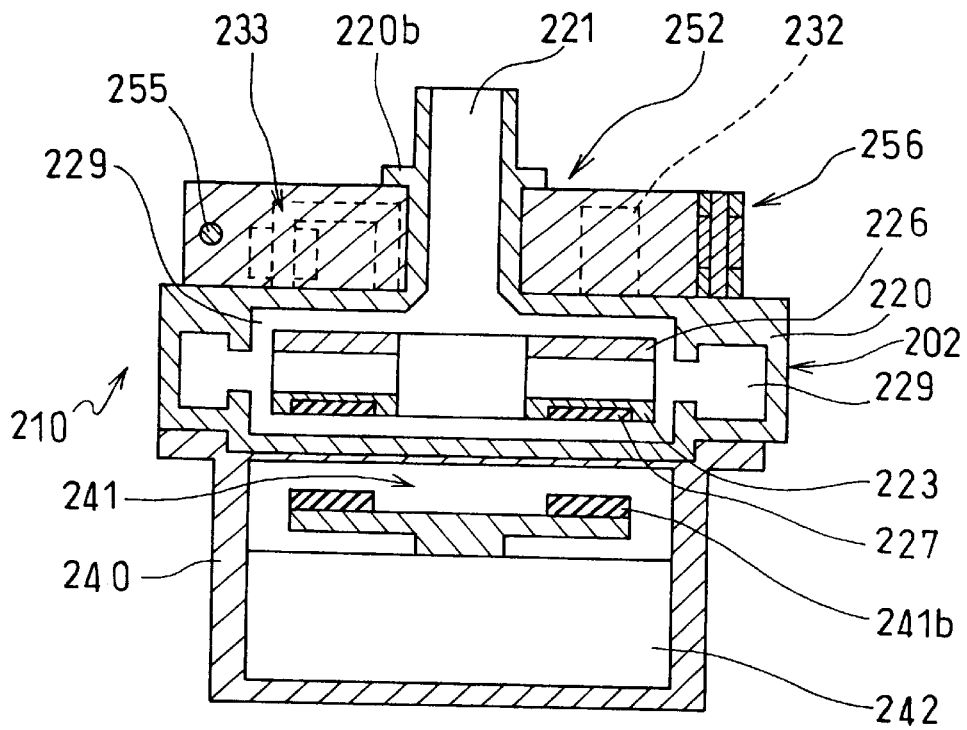
FIG. 23 is a schematic vertical cross-sectional view of a centrifugal blood pump assembly according to a eighth embodiment of the invention.
Figure 24:
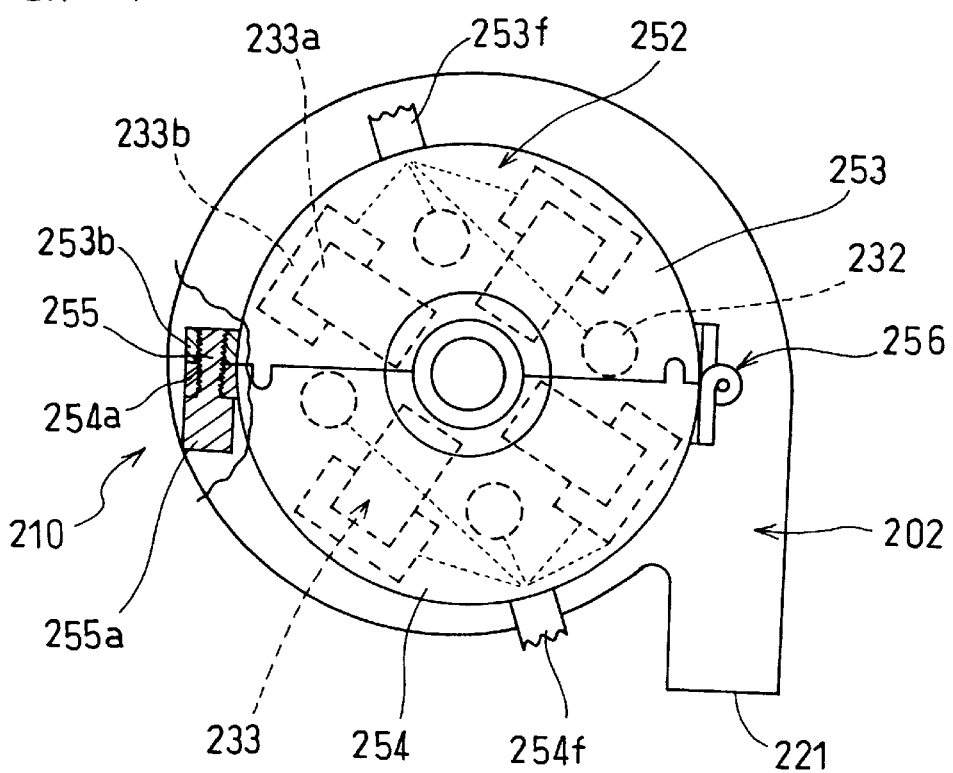
FIG. 24 is a plan view of the pump assembly of FIG. 23 showing one exemplary impeller position control unit.
Figure 25:
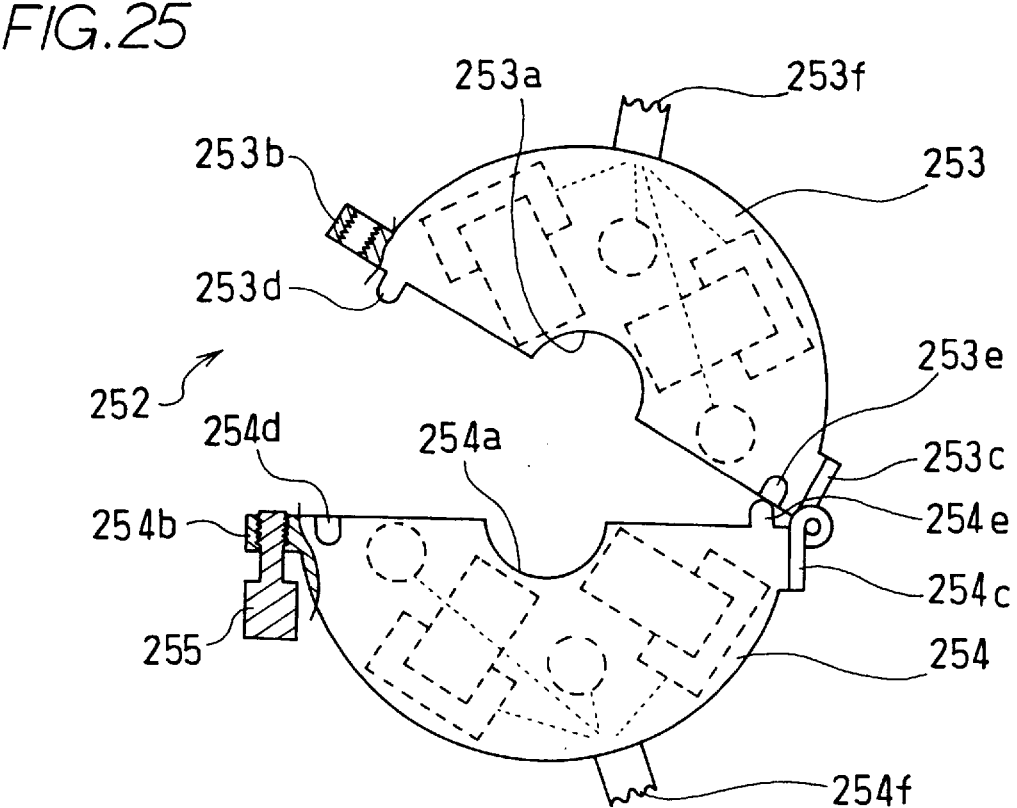
FIG. 25 illustrates the impeller position control unit in a divided state.

Referring to FIGS. 23 to 25, a centrifugal blood pump assembly according to an eighth embodiment of the invention is described. The basic construction of the centrifugal blood pump assembly 210 of this embodiment is the same as that of the centrifugal blood pump assembly 201 shown in FIG. 19. Only the difference is described.

The impeller position control unit 252 is dividable into a plurality of segments, typically two segments. The unit 252 includes a first unit segment 253 and a second unit segment 254 which are substantially semi-circular in plan view. A hinge 256 is secured to the segments 253 and 254 at one diametrical end thereof whereby the segments 253 and 254 are hinge coupled so that the segments may be opened and closed about the hinge 256. When closed, the semi-circular segments mate with each other along their straight side. The segments 253 and 254 are closed or assembled in FIG. 24 and opened or disassembled in FIG. 25. Also as shown in FIGS. 24 and 25, the second segment 254 is provided at another diametrical end with a second fixture 254b having a threaded hole and a screw 255 is in thread engagement with the second fixture 254b. The first segment 253 is also provided at another diametrical end with a first fixture 253b having a threaded hole. More specifically, the first fixture 253b and the second fixture 254b are positioned such that they abut against each other upon assembly. The internal threaded hole of the first fixture is sized to fit with the screw 255. Then, by screwing the screw 255 into the second and first fixtures 254b and 253b, the first and second segments 253 and 254 are held closed as shown in FIG. 24.

As best shown in FIG. 25, the first unit segment 253 is provided at the center of its straight side with a recess 253a for accommodating the inlet port or nozzle and near diametrically opposite ends with a raised knob 253d and a depression 253e. Also the second unit segment 254 is provided at the center of its straight side with a recess 254a for accommodating the inlet port and near diametrically opposite ends with a depression 254d and a raised knob 254e which correspond to the raised knob 253d and the depression 253e of the first segment 253, respectively. These components are provided for the purpose of facilitating assembly of the segments. In the illustrated embodiment wherein the assembled unit has four position detecting sensors 232 and four electromagnets 233, each segment has two position detecting sensors 232 and two electromagnets 233 built therein. Wiring cables 253f and 254f are connected to the first and second segments 253 and 254, respectively.

In this embodiment wherein the impeller position control unit disposed on the side of the blood inlet port of the pump housing is dividable, attachment and detachment of the unit to the pump housing is easier. In particular, even when the impeller position control unit fails during operation, only that unit can be replaced without disconnecting the blood pump from the extracorporeal circulating circuit.

The blood inlet port 221 of the blood pump 202 is provided at an intermediate position with an annular rib 220c as shown in FIG. 23 for preventing the unit 252 from being detached from the blood pump 202 once the unit is assembled and mounted thereon.

Figure 26:
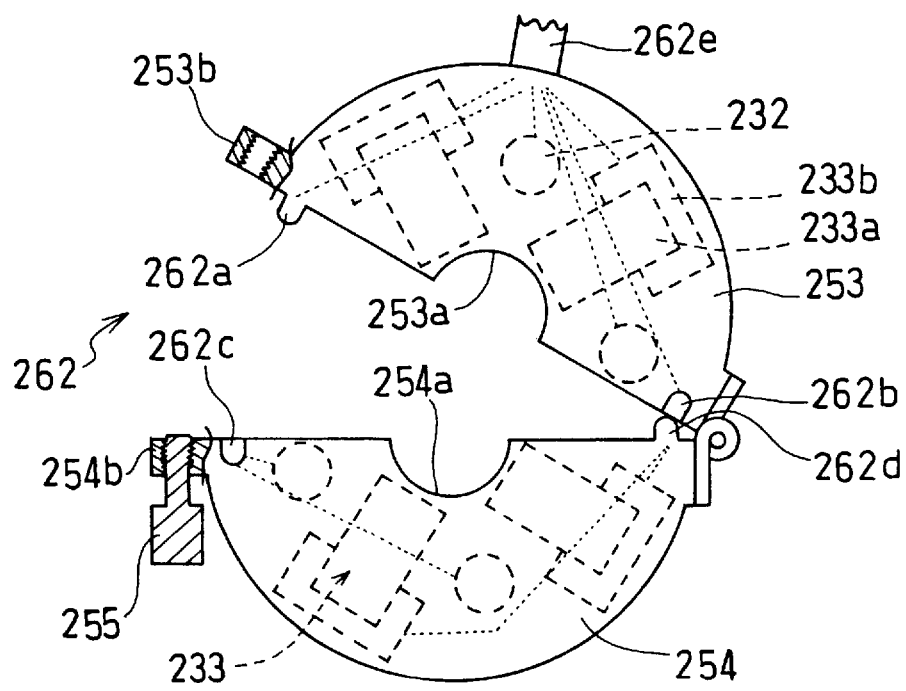
FIG. 26 is a plan view of another exemplary impeller position control unit in a divided state.

FIG. 26 shows another possible configuration of the impeller position control unit. The basic construction of this unit 262 is the same as the above-mentioned unit 252. The difference is that a knob 262a and a corresponding depression 262c and/or a depression 262b and a corresponding knob 262d provided near diametrically opposite ends of the first and second unit segments 253 and 254 are a prong and a socket cooperating as an electric connector. Only one wiring cable 262e is connected to the first segment 253 because an electrical signal in the second segment 254 can be transmitted to the first segment 253 through the electric connector.

This modified embodiment requires electrical wiring to only one of the segments of the impeller position control unit, reducing the number of parts, typically external wiring cables.

Figure 27:
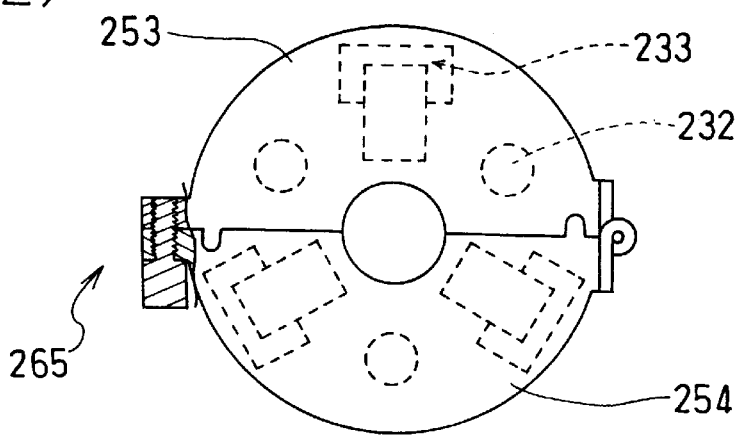
FIG. 27 is a plan view of a further exemplary impeller position control unit in an assembled state.

FIG. 27 shows a further possible configuration of the impeller position control unit. The basic construction of this unit 265 is the same as the above-mentioned unit 252. The difference is that the assembled unit 265 has three position detecting sensors 232 and three electromagnets 233. The three sensors 232 and three electromagnets 233 are distributed on the first and second segments 253 and 254 such that sensors 232 and electromagnets 233 are equiangularly spaced in an assembled state.

Figure 28:
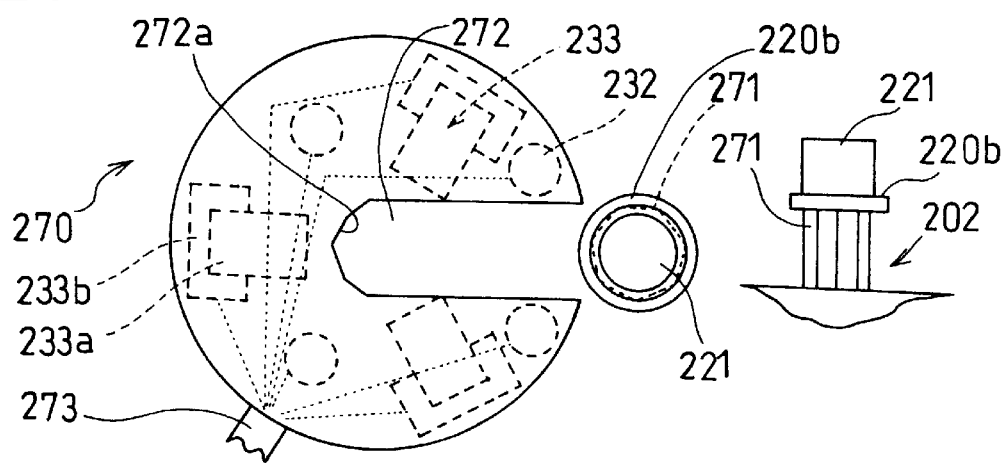
FIG. 28 is a plan view of a still further exemplary impeller position control unit and a portion near the blood inlet port of the blood pump assembly in which the control unit is used.

Referring to FIG. 28, a blood pump assembly according to a still further embodiment of the invention is described. FIG. 28 shows only an impeller position control unit 270 and a portion of the blood pump near the blood inlet port.

As shown in the plan view on the left side of FIG. 28, the unit 270 is provided with a slot 272 radially extending from the center. The slot 272 has a width enough to allow the blood inlet port 221 of the pump housing to be traversed to the center of the unit 270. As shown in the elevational view on the right side of FIG. 28, the inlet port or nozzle 221 is provided at an intermediate position with an annular rib 220c and a lower portion of the inlet port 221 below the rib 220c is a polygonal column, typically octagonal column. The closed end of the slot 272 has a semi-polygonal inside surface 272a corresponding to the polygonal column shape of the lower portion of the inlet port 221. When the unit 270 is mounted to the blood pump, the engagement between the inside surface of the closed end of the slot 272 and the polygonal side surfaces of the lower portion of the inlet port 221 restrains the unit 270 from rotating relative to the pump and the rib 220c restrains the unit 270 from axial motion or detachment from the pump.

Figure 29:
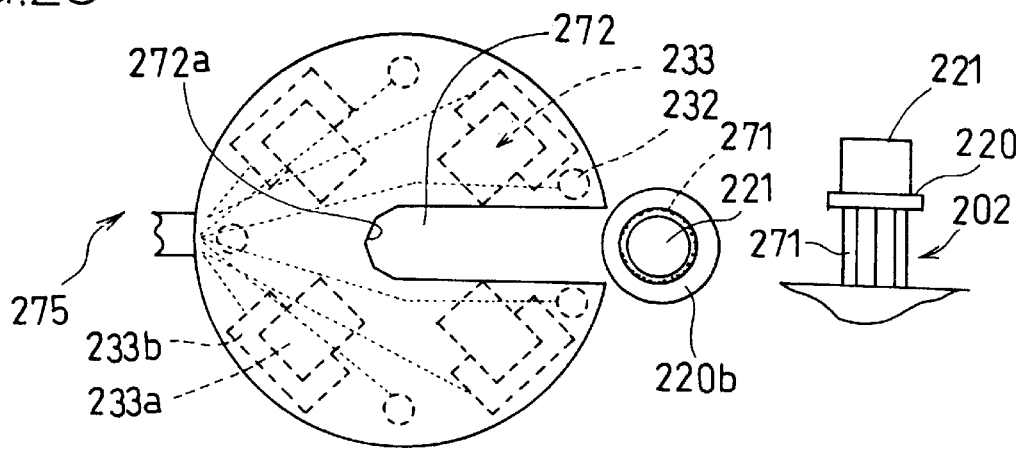
FIG. 29 is a plan view of a yet further exemplary impeller position control unit and a portion near the blood inlet port of the blood pump assembly in which the control unit is used.

The impeller position control unit 270 has three position detecting sensors 232 and three electromagnets 233 arranged at an equiangular spacing in an area other than the slot. Of course, four position detecting sensors 232 and four electromagnets 233 may be arranged at an equiangular spacing as shown in FIG. 29. In these embodiments too, when the impeller position control unit 270 fails during operation, only that unit can be replaced without disconnecting the blood pump from the extracorporeal circulating circuit. In these embodiments, the unit can be easily mounted to and dismounted from the pump simply by laterally moving the unit relative to the inlet port.

Figure 30:
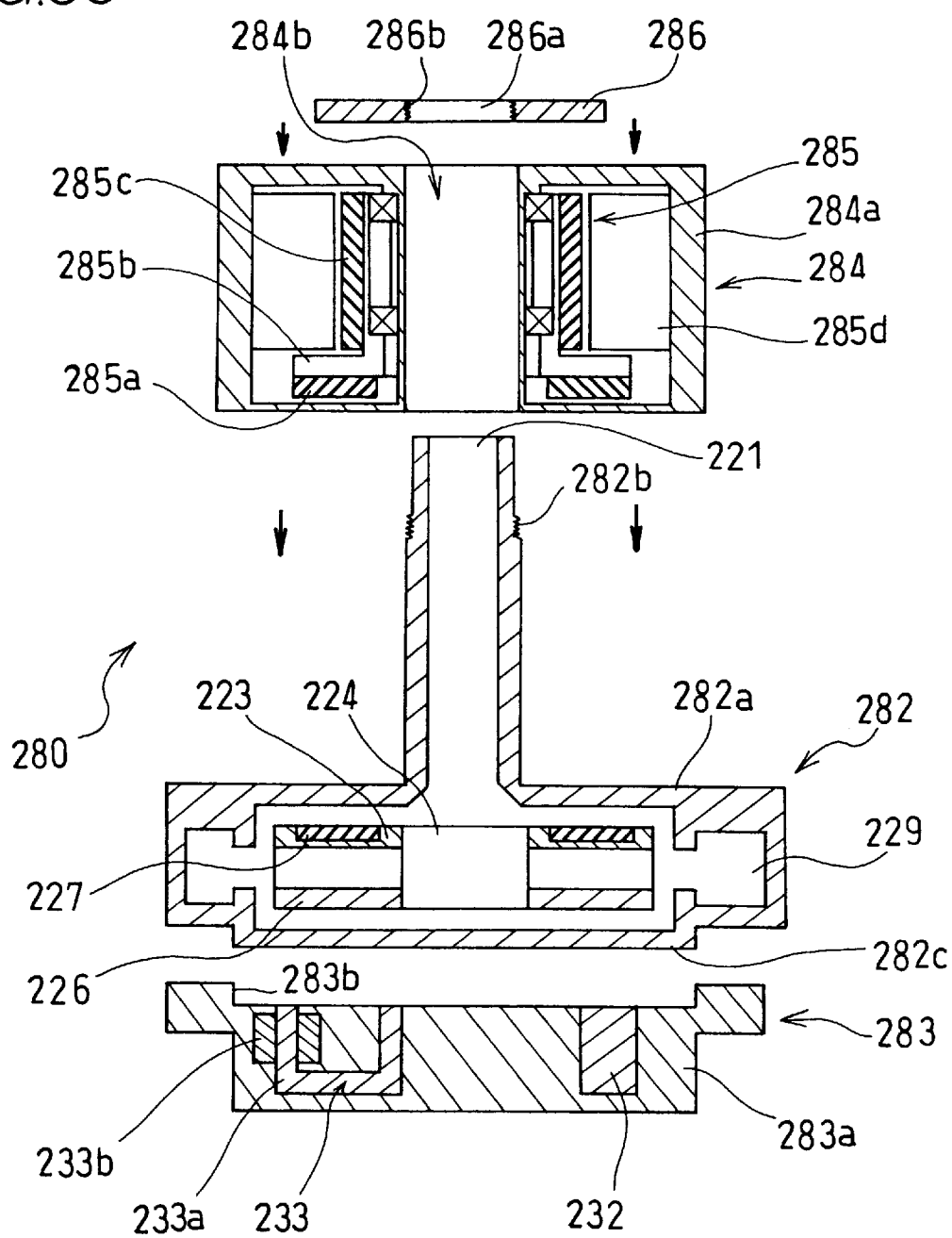
FIG. 30 is a schematic vertical cross-sectional view of a centrifugal blood pump assembly according to a ninth embodiment of the invention in an exploded state.

Referring to FIG. 30, a blood pump assembly according to a yet further embodiment of the invention is described. This blood pump assembly 280 includes a blood pump 282, an impeller position control unit 283, an impeller rotation torque generating unit 284, and an attachment member 286 for securing the unit 284 to the pump 282.

The blood pump 282 is the same as the pump shown in FIGS. 19 to 22 except that external threads 282 formed on the side surface of the blood inlet port 221 are positioned nearer to the blood inlet opening. Briefly stated, the blood pump 282 includes a volute pump housing 282a of non-magnetic material having a blood inlet port 221 and a blood outlet port (not shown) and an impeller 223 received in the housing 282a. The housing 282a defines therein a generally cylindrical chamber or blood flowpath 229 in fluid communication with the inlet and outlet ports. The inlet port 221 on the side surface at a position somewhat below the inlet end is provided with external threads 282b for engagement with internal threads 286b in the attachment member 286. The inlet port 221 protrudes from the top surface of the housing 282a near the center of its generally cylindrical portion in a substantially vertical direction. The outlet port projects from a side surface of the volute housing in a tangential direction. The bottom of the housing 282a is stepped to form a disc-shaped projection 282b for engagement with the impeller position control unit 283. The impeller 223 is the same as the above-mentioned one.

The impeller position control unit 282 is the same as the impeller position control unit 203 shown in FIGS. 19 to 22 except that the center opening through which the inlet port is extended is eliminated and the unit 283 is provided with a disc-shaped recess 283b for engagement with the disc-shaped projection 282b at the bottom of the pump housing 282a. The unit 283 has a plurality of position sensors 232 and electromagnets 233.

The impeller rotation torque generating unit 284 includes a separate housing 284a and an impeller rotation torque generating mechanism 285 received in the housing. The housing 284a is provided with an opening 284b through which the blood inlet port 221 vertically projecting from the housing 282a of the blood pump 282 can be extended. Then the unit 284 can be mounted on the top of the blood pump 282 from above and removed therefrom. When the unit 284 is mounted on the blood pump 282, the external threads 282b on the inlet port 221 extending from the housing 282a of the pump 282 are positioned near the upper surface of the unit 284. Then by fitting the attachment member 286 of a plate shape (typically polygonal plate) having the threaded opening 286b on the inlet port 221 of the housing 282a to provide engagement between threads 286b and 282b, the unit 284 is clamped between the attachment member 286 and the pump 282. Inversely, the unit 284 can be detached from the pump 282 by disengaging the attachment member 286.

The impeller rotation torque generating mechanism 285 includes a cylindrical rotor 285b, a rotor magnet 285c, and a stator coil 285d. The rotor 285b is formed at one end with a flange. A plurality of permanent magnets 285a are attached to one surface of the rotor flange facing the blood pump. The permanent magnets 285a are arranged at an equiangular spacing so as to correspond to the arrangement (number and position) of the permanent magnets 227 in the impeller 223.

Figure 31:
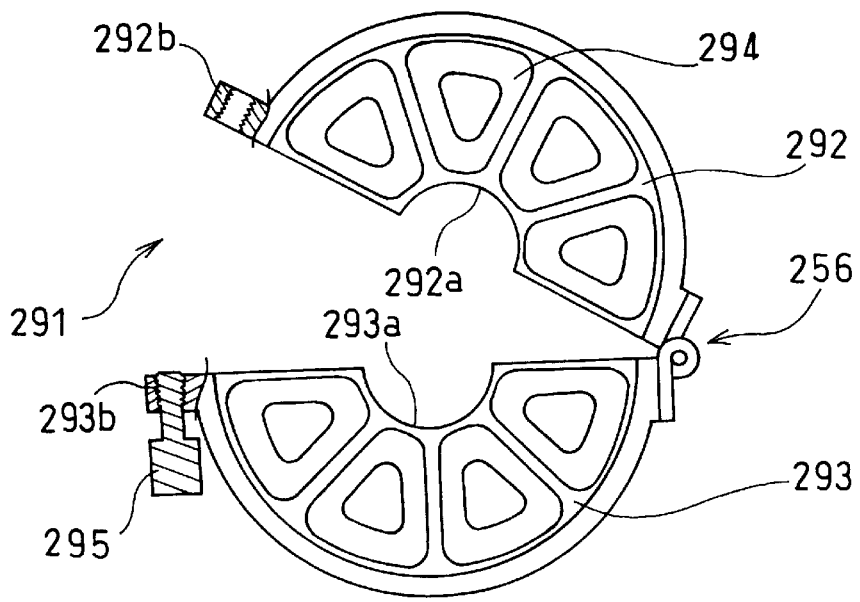
FIG. 31 is a plan view showing an impeller rotational torque generating unit used in the centrifugal blood pump assembly according to the invention in a divided state.
Figure 32:
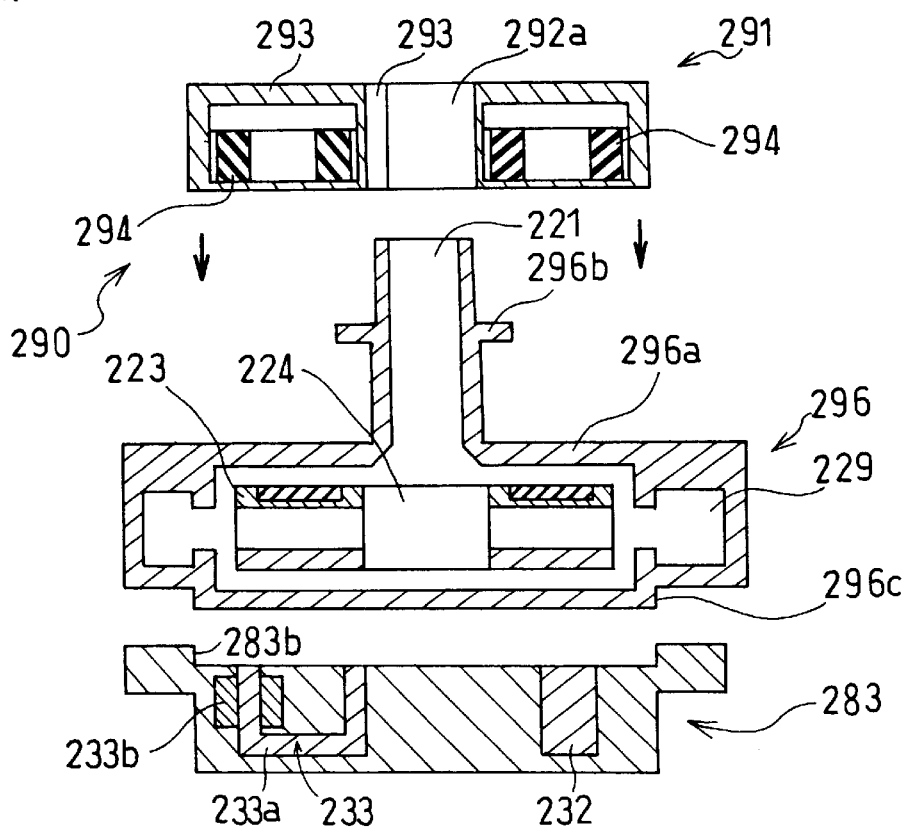
FIG. 32 is a schematic vertical cross-sectional view of a centrifugal blood pump assembly according to a tenth embodiment of the invention in an exploded state.

Referring to FIG. 32, a centrifugal blood pump assembly 290 according to a tenth embodiment of the invention is described. FIG. 31 shows an impeller rotational torque generating unit 291 used in the centrifugal blood pump assembly 290.

This blood pump assembly 290 includes a blood pump 296, an impeller position control unit 283, and an impeller rotational torque generating unit 291.

The blood pump 296 is the same as the above-mentioned pump of FIG. 30 except that the blood inlet port 221 on the side surface is provided at an intermediate position with an annular rib 296b instead of the threads 282. The annular rib 296b prevents the impeller rotational torque generating unit 291 from being detached from the blood pump after it is assembled and mounted thereon. The impeller 223 is the same as the above-mentioned one. The impeller position control unit 282 is the same as the above-mentioned unit of FIG. 30.

The impeller rotational torque generating unit 291 includes a plurality of stator coils 294 for driving the impeller for rotation while attracting the permanent magnet of the impeller. Since the use of such a flat brushless motor mechanism omits any movable member from within the rotational torque generating unit 291, the unit has a physically dividable structure. That is, the unit 291 has a structure divided into a plurality of, typically two, segments. The unit 291 is divided into a first unit segment 292 and a second unit segment 293 which are semi-circular shaped in plan view as shown in FIG. 31. A hinge 256 is secured to the segments 292 and 293 at one diametrical end thereof whereby the segments 292 and 293 are hinge coupled so that the segments may be opened and closed about the hinge 256. When closed, the semi-circular segments mate with each other along their straight side. The segments 292 and 293 are opened or disassembled in FIG. 31.

The first unit segment 292 is provided at the center of its straight side with a recess 292a for accommodating the inlet port. Similarly the second unit segment 293 is provided at the center of its straight side with a recess 293a for accommodating the inlet port. Also, the second segment 293 is provided at another diametrical end with a second fixture 293b having a threaded hole and a screw 295 is in thread engagement with the second fixture 293b. The first segment 292 is also provided at another diametrical end with a first fixture 292b having a threaded hole. More specifically, the first fixture 292b and the second fixture 293b are positioned such that they abut against each other upon assembly. The internal threaded hole of the first fixture is sized to fit with the screw 295. Then, by screwing the screw 295 into the second and first fixtures 293b and 292b, the first and second segments 292 and 293 are held closed.

In this embodiment wherein the impeller rotation torque generating unit disposed adjacent the blood inlet port of the pump housing is dividable, attachment and detachment of the unit to the pump housing is easier. In particular, even when the impeller rotation torque generating unit fails during operation, only that unit can be replaced without disconnecting the blood pump from the extracorporeal circulating circuit.

Figure 33:
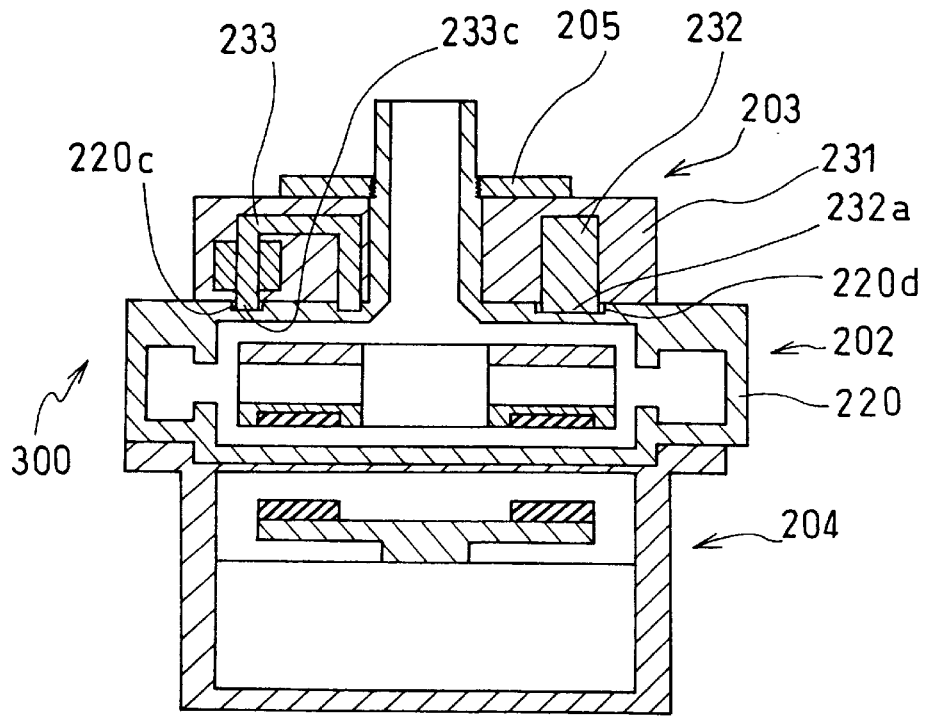
FIG. 33 is a schematic vertical cross-sectional view of a centrifugal blood pump assembly according to an eleventh embodiment of the invention.
Figure 34:
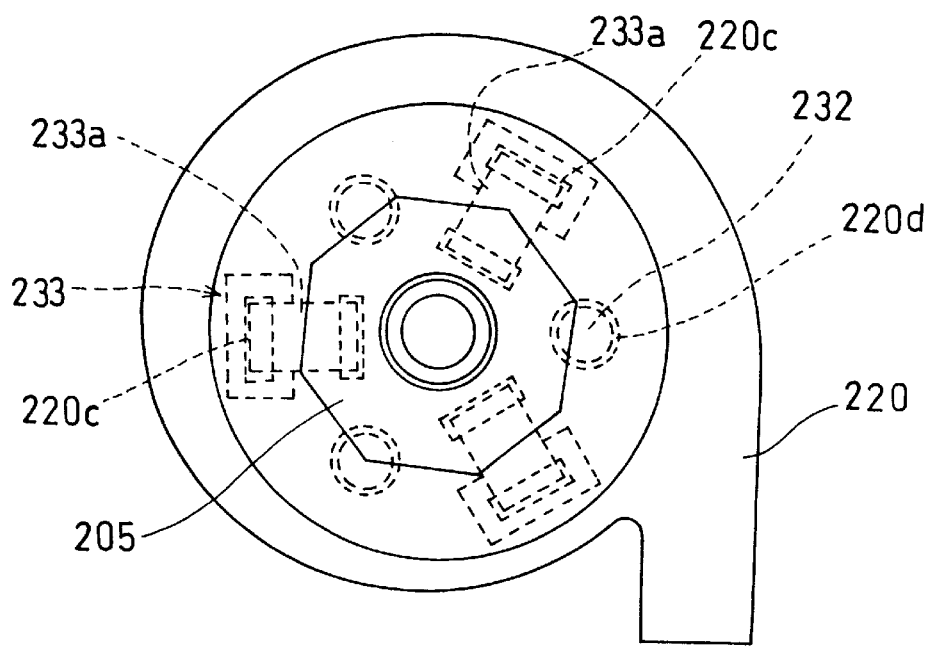
FIG. 34 is a plan view of the pump of FIG. 33.

Referring to FIGS. 33 and 34, a centrifugal blood pump assembly according to an eleventh embodiment of the invention.

The basic construction of this blood pump assembly 300 is the same as the blood pump assembly 201 shown in FIGS. 19 to 22. The only difference is the configuration of abutment between the impeller position control unit 203 and the blood pump 202. In the unit 203 of the blood pump assembly 300, a plurality of (typically three) of position sensors 232 and a plurality of (typically three) electromagnets 233 are disposed in a separate housing 231 such that the lower end 232a of the sensors 232 and the lower end 233c of the electromagnets 233 (specifically the lower end of the cores) are projected downward beyond the lower surface of the housing 231. In conjunction with this projection, the blood pump 202 is provided on the top surface with recesses 220c for receiving the lower end 233c of the electromagnets 233 and recesses 220d for receiving the lower end 232a of the sensors 232. Engagement between these projections and recesses prevents the unit 203 from being loosened after it is mounted on the blood pump. Additionally, the distance between the lower end of the electromagnet cores and the magnetic member of the impeller is reduced to ensure that the electromagnets magnetically attract the impeller.

Although the means for securing the impeller position control unit and torque generating unit to the pump housing is thread engagement and the means for coupling divided segments of the impeller position control unit and torque generating unit is hinge engagement in the foregoing embodiments, the securing means and the coupling means are not limited thereto. Latch mechanisms and other well-known securing and coupling means may be used.

In the first aspect, the centrifugal blood pump assembly comprises a centrifugal blood pump comprising a housing having an inlet port and an outlet port for blood and adapted to receive blood therein, and an impeller rotatable in the housing for feeding blood by a centrifugal force developed during rotation; controlled magnetic bearing means for magnetically supporting the impeller; and uncontrolled magnetic bearing means for magnetically supporting the impeller. The controlled magnetic bearing means and the uncontrolled magnetic bearing means cooperate such that the impeller rotates while it is held at a predetermined position within the housing. The impeller is rotatable even when the controlled magnetic bearing means is inoperative and the uncontrolled magnetic bearing means is operative. During rotation of the impeller, a blood flowpath is defined between a surface of the impeller on the side of the uncontrolled magnetic bearing means and an inner surface of the housing facing the impeller surface. Then, the impeller rotates by virtue of the uncontrolled magnetic bearing means even when the controlled magnetic bearing means is inoperative. That is, the pump assembly is fail-safe. During rotation of the impeller enabled by the fail-safe mechanism, the blood flowpath is maintained to prevent blood stagnation between the lower surface of the impeller and the opposed bottom inner surface of the housing, minimizing thrombus formation.

In the second aspect, the centrifugal blood pump assembly comprises a centrifugal blood pump comprising a housing having an inlet port and an outlet port for blood and adapted to receive blood therein, and an impeller adapted to rotate within the housing for feeding blood by a centrifugal force developed during rotation; a controlled magnetic bearing means for magnetically supporting the impeller; and an uncontrolled magnetic bearing means for magnetically supporting the impeller. The controlled magnetic bearing means and the uncontrolled magnetic bearing means cooperate such that the impeller rotates while it is held at a predetermined position within the housing. The impeller is rotatable even when the controlled magnetic bearing means is inoperative and the uncontrolled magnetic bearing means is operative. The impeller includes an opening extending through the impeller at the center and a beveled edge at the crossing of the opening with the surface of the impeller facing the uncontrolled magnetic bearing means, the beveled edge increasing its diameter toward the uncontrolled magnetic bearing means. The housing includes a raised portion formed on the inner surface at a position corresponding to the opening of the impeller, the raised portion having a tapered side surface which comes in contact with the beveled edge of the impeller when the controlled magnetic bearing means is inoperative. Then, the impeller rotates by virtue of the uncontrolled magnetic bearing means even when the controlled magnetic bearing means is inoperative. That is, the pump assembly is failsafe. During rotation of the impeller enabled by the fail-safe mechanism, no contact occurs between the lower surface of the impeller and the opposed bottom inner surface of the housing. Instead, substantial plane contact occurs between the beveled edge of the impeller and the tapered side surface of the raised portion on the housing. In this state, the impeller rotates without causing the impeller outer edge to contact any inner surface of the housing. Stable rotation of the impeller is thus ensured.

In the third aspect, the centrifugal blood pump assembly comprises a centrifugal blood pump comprising a housing having an inlet port and an outlet port for blood and adapted to receive blood therein, and an impeller adapted to rotate within the housing for feeding blood by a centrifugal force developed during rotation; a controlled magnetic bearing means for magnetically supporting the impeller; and an uncontrolled magnetic bearing means for magnetically supporting the impeller. The controlled magnetic bearing means and the uncontrolled magnetic bearing means cooperate such that the impeller rotates while it is held at a predetermined position within the housing. The controlled magnetic bearing means and the uncontrolled magnetic bearing means are removably mounted to the blood pump. In this pump assembly, the impeller rotates in a substantially non-contact state for feeding blood. The non-contact rotation eliminates the physical influence on corpuscles, more specifically damage to erythrocytes and platelets. After use, only the blood pump section is discarded while the controlled magnetic bearing means or impeller position control unit and the uncontrolled magnetic bearing means or impeller rotation torque generating unit are reusable. The invention is commensurate with the social requirement to reduce the amount of medical instruments discarded as industrial waste.

Although some preferred embodiments have been described, many modifications and variations may be made thereto in the light of the above teachings. It is therefore to be understood that within the scope of the appended claims, the invention may be practiced otherwise than as specifically described.

We claim:

1. A centrifugal blood pump assembly comprising
   a centrifugal blood pump comprising a housing having an inlet port and an outlet port for blood and adapted to receive blood therein, and an impeller rotatable in said housing for feeding blood by a centrifugal force developed during rotation,
   a controlled magnetic bearing means for magnetically supporting said impeller, and
   an uncontrolled magnetic bearing means for magnetically supporting said impeller, wherein
   said controlled magnetic bearing means and said uncontrolled magnetic bearing means cooperate such that said impeller rotates while it is held at a predetermined position within said housing,
   said centrifugal blood pump has a blood flowpath defined between a surface of said impeller on a side of said uncontrolled magnetic bearing means and an inner surface of said housing facing said impeller surface when said controlled magnetic bearing means is inoperative and said uncontrolled magnetic bearing means is operative, and
   said impeller is rotatable even when said controlled magnetic bearing means is inoperative and said uncontrolled magnetic bearing means is operative.

2. The centrifugal blood pump assembly of claim 1 wherein said impeller includes a magnetic member disposed on one surface and a permanent magnet disposed on another surface of the impeller.

3. The centrifugal blood pump assembly of claim 1 wherein said impeller has ribs which come in contact with said inner surface of said housing when said controlled magnetic bearing means is inoperative.

4. The centrifugal blood pump assembly of claim 1 wherein said inner surface of said housing has ribs which come in contact with said impeller when said controlled magnetic bearing means is inoperative.

5. The centrifugal blood pump assembly of claim 3 wherein said impeller has at least three ribs.

6. The centrifugal blood pump assembly of claim 1 wherein
   said impeller includes a recess formed substantially at the center of its surface facing said uncontrolled magnetic bearing means and
   said housing has a raised portion formed on said inner surface at a position corresponding to the recess or said impeller, the raised portion making pivotal engagement with the recess for providing pivotal support to the impeller.

7. The centrifugal blood pump assembly of claim 1 wherein
   said impeller includes a small diameter through-hole formed substantially at the center of its surface facing said uncontrolled magnetic bearing means and
   said housing has a raised portion formed on said inner surface at a position corresponding to the through-hole of said impeller, the raised portion projecting into the through-hole to make pivotal engagement with the through-hole for providing pivotal support to the impeller.

8. The centrifugal blood pump assembly of claim 1 wherein said impeller has hydrodynamic grooves formed in its surface facing said uncontrolled magnetic bearing means whereby said impeller rotates without contact with any portion of the housing due to the hydrodynamic bearing effect developed between the hydrodynamic grooves and said housing inner surface when said controlled magnetic bearing means is inoperative and said uncontrolled magnetic bearing means is operative.

9. The centrifugal blood pump assembly of claim 2 wherein said controlled magnetic bearing means is an impeller position control section including a stationary electromagnet for magnetically attracting the magnetic member of said impeller and a position sensor for detecting the position of the magnetic member of said impeller.

10. The centrifugal blood pump assembly of claim 2 wherein said uncontrolled magnetic bearing means is an impeller rotation torque generating section including a rotor having a permanent magnet for magnetically attracting the permanent magnet of said impeller and a motor for rotating said rotor.

11. The centrifugal blood pump assembly of claim 2 wherein said uncontrolled magnetic bearing means is an impeller rotation torque generating section including a plurality of stator coils for driving said impeller for rotation while magnetically attracting the permanent magnet of said impeller.

12. A centrifugal blood pump assembly comprising
    a centrifugal blood pump comprising a housing having an inlet port and an outlet port for blood and adapted to receive blood therein, and an impeller adapted to rotate within the housing for feeding blood by a centrifugal force developed during rotation, a controlled magnetic bearing means for magnetically supporting said impeller, and an uncontrolled magnetic bearing means for magnetically supporting said impeller, wherein said controlled magnetic bearing means and said uncontrolled magnetic bearing means cooperate such that said impeller rotates while it is held at a predetermined position within said housing, said impeller is rotatable even when said controlled magnetic bearing means is inoperative and said uncontrolled magnetic bearing means is operative, said impeller includes an opening extending through the impeller at the center and a beveled edge at the crossing of the opening with the surface of said impeller facing said uncontrolled magnetic bearing means, the beveled edge increasing its diameter toward said uncontrolled magnetic bearing means, and said housing includes a raised portion formed on said inner surface at a position corresponding to the opening of said impeller, the raised portion having a tapered side surface which comes in contact with the beveled edge of said impeller when said controlled magnetic bearing means is inoperative.

13. The centrifugal blood pump assembly of claim 12 wherein said impeller includes a magnetic member disposed on one surface and a permanent magnet disposed on another surface of said impeller.

14. The centrifugal blood pump assembly of claim 12 wherein a blood flowpath is defined between a surface of the impeller on the side of said uncontrolled magnetic bearing means and an inner surface of the housing facing the impeller surface during rotation of said impeller when said controlled magnetic bearing means is inoperative and said uncontrolled magnetic bearing means is operative.

15. The centrifugal blood pump assembly of claim 14 wherein the beveled edge of said impeller or the raised portion on the inner surface of said housing is provided with grooves for ensuring blood flow communication between said impeller and said housing during rotation of said impeller when said controlled magnetic bearing means is inoperative and said uncontrolled magnetic bearing means is operative.

16. The centrifugal blood pump assembly of claim 13 wherein said controlled magnetic bearing means is an impeller position control section including a stationary electromagnet for magnetically attracting the magnetic member of said impeller and a position sensor for detecting the position of the magnetic member of said impeller.

17. The centrifugal blood pump assembly of claim 13 wherein said uncontrolled magnetic bearing means is an impeller rotation torque generating section including a rotor having a permanent magnet for magnetically attracting the permanent magnet of said impeller and a motor for rotating said rotor.

18. The centrifugal blood pump assembly of claim 13 wherein said uncontrolled magnetic bearing means is an impeller rotation torque generating section including a plurality of stator coils for driving said impeller for rotation while magnetically attracting the permanent magnet of said impeller.

19. A centrifugal blood pump assembly comprising a centrifugal blood pump comprising a blood pump housing having an inlet port and an outlet port for blood and adapted to receive blood therein, and an impeller adapted to rotate within the housing for feeding blood by a centrifugal force developed during rotation, an impeller position control unit for magnetically supporting said impeller including a control unit housing separable from said blood pump housing, an electromagnet positioned in the control unit housing and a position sensor positioned in the control unit housing, and an impeller rotation torque generating unit including a torque generating unit housing separable from the blood pump housing and an impeller rotation torque generating mechanism in the torque generating unit housing, wherein said impeller position control unit and the impeller rotation torque generating unit cooperate such that said impeller rotates while it is held at a predetermined position within said blood pump housing, and said impeller position control unit and the impeller rotation torque generating unit are removably mounted to said centrifugal blood pump.

20. The centrifugal blood pump assembly of claim 19 wherein said impeller includes a magnetic member disposed on one surface and a permanent magnet disposed on another surface of said impeller.

21. The centrifugal blood pump assembly of claim 20 wherein said impeller position control unit includes a stationary electromagnet for magnetically attracting the magnetic member of said impeller and said position sensor for detecting the position of the magnetic member of said impeller.

22. The centrifugal blood pump assembly of claim 20 wherein the electromagnet and/or the position sensor of said impeller position control unit has a lower end which forms an outward projection and an outer surface of said housing of said blood pump facing said impeller position control unit has a recess for receiving the outward projection.

23. The centrifugal blood pump assembly of claim 20 wherein said impeller rotation torque generating unit includes a rotor having a permanent magnet for magnetically attracting the permanent magnet of said impeller and a motor for rotating said rotor.

24. The centrifugal blood pump assembly of claim 20 wherein said uncontrolled magnetic bearing means is an impeller rotation torque generating unit including a plurality of stator coils for driving said impeller for rotation while magnetically attracting the permanent magnet of said impeller.

25. The centrifugal blood pump assembly of claim 19 wherein one of said impeller position control unit and said impeller rotation torque generating unit that is mounted to the blood pump adjacent its blood inlet passage has a structure which is dividable into a plurality of segments.

26. The centrifugal blood pump assembly of claim 25 wherein said impeller position control unit consists of a plurality of segments which have a raised portion and a depression which are mated together upon assembly, the raised portion and the depression also having a function of an electric connector.

27. The centrifugal blood pump assembly of claim 21 wherein either one of said impeller position control unit and said impeller rotation torque generating unit has an opening through which the blood inlet port projecting substantially vertically from the housing of said blood pump substantially at the center thereof is extendible.

28. The centrifugal blood pump assembly of claim 27 wherein said either one unit is mountable to said blood pump by moving said unit from above the blood inlet port such that the blood inlet port is inserted into the opening.

29. The centrifugal blood pump assembly of claim 21 further comprising an attachment member having an internally threaded opening, wherein said blood inlet port on the side surface is provided with external threads sized to be in thread engagement with the internally threaded opening of said attachment member, and either one of said impeller position control unit and said impeller rotation torque generating unit is removably secured by clamping the unit between said blood pump and said attachment member.

30. The centrifugal blood pump assembly of claim 4 wherein said impeller has at least three ribs.

31. The centrifugal blood pump assembly of claim 2 wherein said impeller includes a recess formed substantially at the center of its surface facing said uncontrolled magnetic bearing means and said housing has a raised portion formed on said inner surface at a position corresponding to the recess of said impeller, the raised portion making pivotal engagement with the recess for providing pivotal support to the impeller.

32. The centrifugal blood pump assembly of claim 8 wherein said controlled magnetic bearing means is an impeller position control section including a stationary electromagnet for magnetically attracting the magnetic member of said impeller and a position sensor for detecting the position of the magnetic member of said impeller.

33. The centrifugal blood pump assembly of claim 9 wherein said uncontrolled magnetic bearing means is an impeller rotation torque generating section including a rotor having a permanent magnet for magnetically attracting the permanent magnet of said impeller and a motor for rotating said rotor.

34. The centrifugal blood pump assembly of claim 9 wherein said uncontrolled magnetic bearing means is an impeller rotation torque generating section including a plurality of stator coils for driving said impeller for rotation while magnetically attracting the permanent magnet of said impeller.

35. The centrifugal blood pump assembly of claim 13 wherein a blood flowpath is defined between a surface of the impeller on the side of said uncontrolled magnetic bearing means and an inner surface of the housing facing the impeller surface during rotation of said impeller when said controlled magnetic bearing means is inoperative and said uncontrolled magnetic bearing means is operative.

36. The centrifugal blood pump assembly of claim 15 wherein said controlled magnetic bearing means is an impeller position control section including a stationary electromagnet for magnetically attracting the magnetic member of said impeller and a position sensor for detecting the position of the magnetic member of said impeller.

37. The centrifugal blood pump assembly of claim 16 wherein said uncontrolled magnetic bearing means is an impeller rotation torque generating section including a rotor having a permanent magnet for magnetically attracting the permanent magnet of said impeller and a motor for rotating said rotor.

38. The centrifugal blood pump assembly of claim 16 wherein said uncontrolled magnetic bearing means is an impeller rotation torque generating section including a plurality of stator coils for driving said impeller for rotation while magnetically attracting the permanent magnet of said impeller.

39. The centrifugal blood pump assembly of claim 22 wherein said uncontrolled magnetic bearing means is an impeller rotation torque generating unit including a rotor having a permanent magnet for magnetically attracting the permanent magnet of said impeller and a motor for rotating said rotor.

40. The centrifugal blood pump assembly of claim 22 wherein said uncontrolled magnetic bearing means is an impeller rotation torque generating unit including a plurality of stator coils for driving said impeller for rotation while magnetically attracting the permanent magnet of said impeller.

41. The centrifugal blood pump assembly of claim 26 wherein either one of said impeller position control unit and said impeller rotation torque generating unit has an opening through which the blood inlet port projecting substantially vertically from the housing of said blood pump substantially at the center thereof is extendible.

42. The centrifugal blood pump assembly of claim 28 further comprising an attachment member having an internally threaded opening, wherein said blood inlet port on the side surface is provided with external threads sized to be in thread engagement with the internally threaded opening of said attachment member, and either one of said impeller position control unit and said impeller rotation torque generating unit is removably secured by clamping the unit between said blood pump and said attachment member.

43. The centrifugal blood pump assembly of claim 19, wherein said impeller position control unit is provided with a slot extending radially from the center having a width sufficient to accommodate said blood inlet port of said pump housing.

* * * * *

UNITED STATES PATENT AND TRADEMARK OFFICE
CERTIFICATE OF CORRECTION

PATENT NO. : 5,947,703
DATED : September 7, 1999
INVENTOR(S) : Toshihiko NOJIRI et al It is certified that error appears in the above-indentified patent and that said Letters Patent is hereby corrected as shown below:

In Column 5, line 51, delete "5" and insert -- 51 --.
In Column 6, line 24, delete "5*a*" and insert -- 51*a* --.
In Column 10, line 65, delete "101 a" and insert -- 101*a* --.
In Column 16, line 20, delete "282" and insert -- 283 --.
In Column 17, line 5, delete "282" and insert -- 283 --.

Signed and Sealed this

Seventeenth Day of October, 2000

Q. TODD DICKINSON

Attest:

Attesting Officer

Director of Patents and Trademarks